US012588852B2

(12) United States Patent (10) Patent No.: US 12,588,852 B2
Eminoglu et al. (45) Date of Patent: Mar. 31, 2026

(54) NEURAL INTERFACE SYSTEM AND METHOD

(71) Applicant: Science Corporation, Alameda, CA (US)

(72) Inventors: Selim Eminoglu, Alameda, CA (US); Max Rothman, Alameda, CA (US)

(73) Assignee: Science Corporation, Alameda, CA (US)

( * ) Notice: Subject to any disclaimer, the term of this patent is extended or adjusted under 35 U.S.C. 154(b) by 0 days.

(21) Appl. No.: 19/097,738

(22) Filed: Apr. 1, 2025

(65) Prior Publication Data

US 2025/0306681 A1 Oct. 2, 2025

Related U.S. Application Data

(60) Provisional application No. 63/572,837, filed on Apr. 1, 2024.

(51) Int. Cl.
*A61B 5/294* (2021.01)
*A61B 5/30* (2021.01)
*G06F 3/01* (2006.01)

(52) U.S. Cl.
CPC ............... *A61B 5/294* (2021.01); *A61B 5/30* (2021.01); *G06F 3/015* (2013.01)

(58) Field of Classification Search
CPC ............ A61B 5/294; A61B 5/30; G06F 3/015
See application file for complete search history.

(56) References Cited

U.S. PATENT DOCUMENTS

| | | | |
|---|---|---|---|
| 9,477,640 B2 | 10/2016 | Yang et al. | |
| 10,722,729 B2 * | 7/2020 | Deligianni | ............... A61B 5/24 |
| 10,937,407 B2 | 3/2021 | Goldstein | |

(Continued)

FOREIGN PATENT DOCUMENTS

| | | |
|---|---|---|
| CN | 114668409 A | 6/2022 |
| WO | 2015183690 A1 | 12/2015 |
| WO | 2023129840 A1 | 7/2023 |

OTHER PUBLICATIONS

Rostov, et al., "Brian-Computer Interface System and Method", Co-pending U.S. Appl. No. 19/336,033, filed Sep. 22, 2025.

(Continued)

*Primary Examiner* — Michael Pervan
(74) *Attorney, Agent, or Firm* — Jeffrey Schox; Annabel Imbrie-Moore

(57) ABSTRACT

The system (e.g., neural interface system) can include: one or more recording modules and/or one or more stimulus modules. In an example, the system can include an electrical recording module and an optical stimulus module. In an example, the electrical recording module can include: a neural interface module, a digital controller module, an analog drive module, and/or an electrode multiplexer. In a specific example, the optical stimulus module can include: a LED driver IC and set of LEDs, where the LED driver IC provides required power and control signals to run the set of LEDs and set of LEDs apply desired optical stimulus to a set of neurons. In variants, the system can function to read signals from neurons (e.g., reading electrical signals via electrodes) and/or transmit signals to neurons (e.g., transmitting electrical signals via electrodes and/or transmitting light signals via LEDs).

19 Claims, 16 Drawing Sheets

(56) References Cited

U.S. PATENT DOCUMENTS

| | | |
|---|---|---|
| 2003/0130616 A1 | 7/2003 | Steil et al. |
| 2005/0090756 A1 | 4/2005 | Wolf et al. |
| 2009/0157141 A1 | 6/2009 | Chiao et al. |
| 2013/0030352 A1 | 1/2013 | Seymour et al. |
| 2014/0094674 A1 | 4/2014 | Nurmikko et al. |
| 2016/0143555 A1 | 5/2016 | Deere |
| 2016/0228705 A1 | 8/2016 | Crowder et al. |
| 2017/0215940 A1 | 8/2017 | Hill et al. |
| 2018/0039328 A1 | 2/2018 | Malik et al. |
| 2019/0366094 A1 | 12/2019 | Esteller |
| 2020/0155019 A1 | 5/2020 | Esteller et al. |
| 2022/0167901 A1 | 6/2022 | Park et al. |
| 2023/0077899 A1* | 3/2023 | Mardinly .............. A61L 27/383 623/23.72 |
| 2023/0285742 A1 | 9/2023 | Rapoport et al. |
| 2024/0134452 A1 | 4/2024 | Shull et al. |
| 2025/0114635 A1* | 4/2025 | Xu ........................ A61N 5/0622 |
| 2025/0302358 A1 | 10/2025 | Eminoglu |
| 2025/0303127 A1* | 10/2025 | Browd ................... A61N 5/062 |
| 2025/0366759 A1* | 12/2025 | Peng ..................... A61B 5/293 |

OTHER PUBLICATIONS

Shihada, J. Abu, "Highly Customizable 30 Microelectrode Arrays for In Vitro and In Vivo Neuronal Tissue Recordings", Advanced Science, 11, 202305944, 2024.

\* cited by examiner

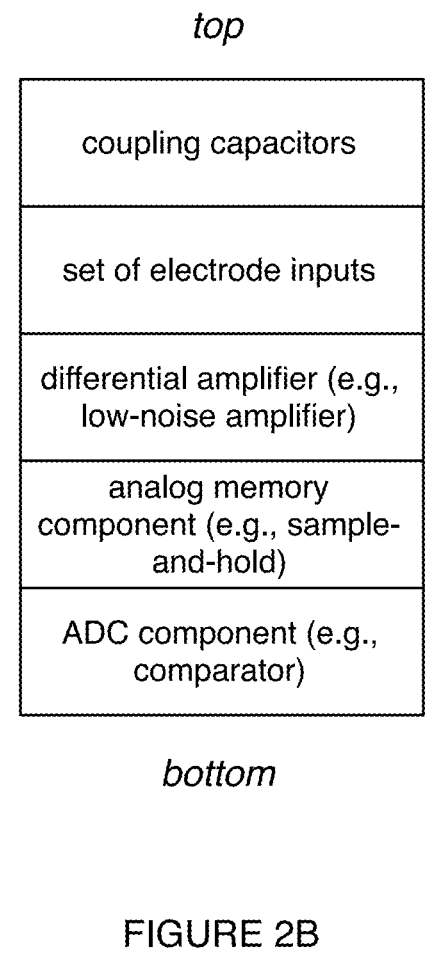

*top*

| coupling capacitors |
| :---: |
| set of electrode inputs |
| differential amplifier (e.g., low-noise amplifier) |
| analog memory component (e.g., sample-and-hold) |
| ADC component (e.g., comparator) |

*bottom*

FIGURE 2B

| | = pair of active electrode input 0 and active electrode input 1 |
| | = pair of passive electrode input 0 and passive electrode input 1 |

NEURAL INTERFACE SYSTEM AND METHOD

CROSS-REFERENCE TO RELATED APPLICATIONS

This application claims the benefit of U.S. Provisional Application No. 63/572,837 filed 1 Apr. 2024, which is incorporated in its entirety by this reference.

TECHNICAL FIELD

This invention relates generally to the integrated circuit field, and more specifically to a new and useful neural interface system and method in the integrated circuit field.

BRIEF DESCRIPTION OF THE FIGURES

FIG. 2B depicts an example arrangement of components of a neural interface element ("nixel").

DETAILED DESCRIPTION

The following description of the embodiments of the invention is not intended to limit the invention to these embodiments, but rather to enable any person skilled in the art to make and use this invention.

1. Overview

Figure 1A:
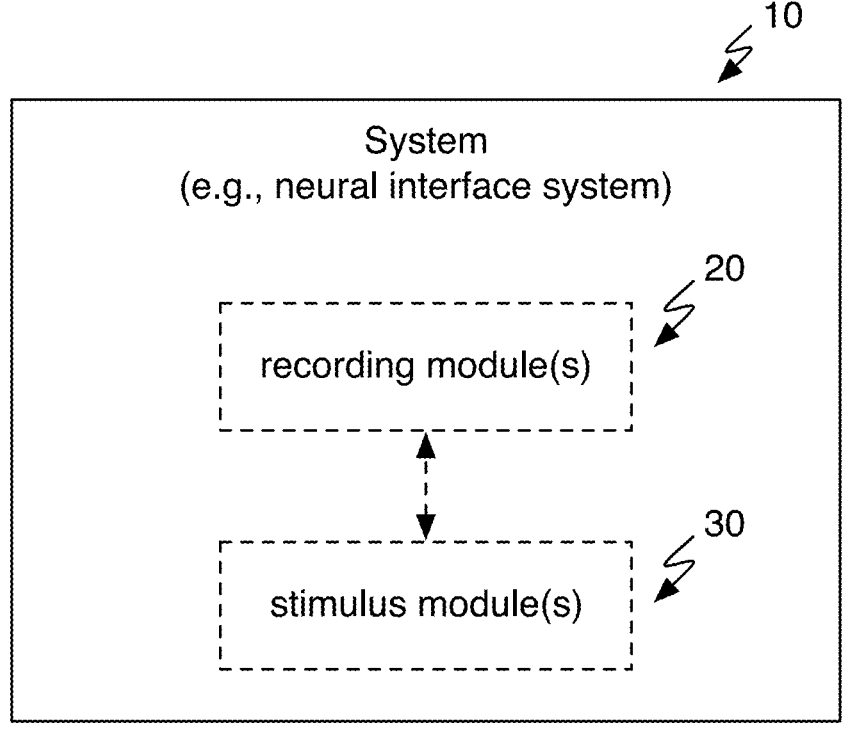
FIG. 1A is a schematic representation of a variant of the system, including a recording module and an optional stimulus module.
Figure 1B:
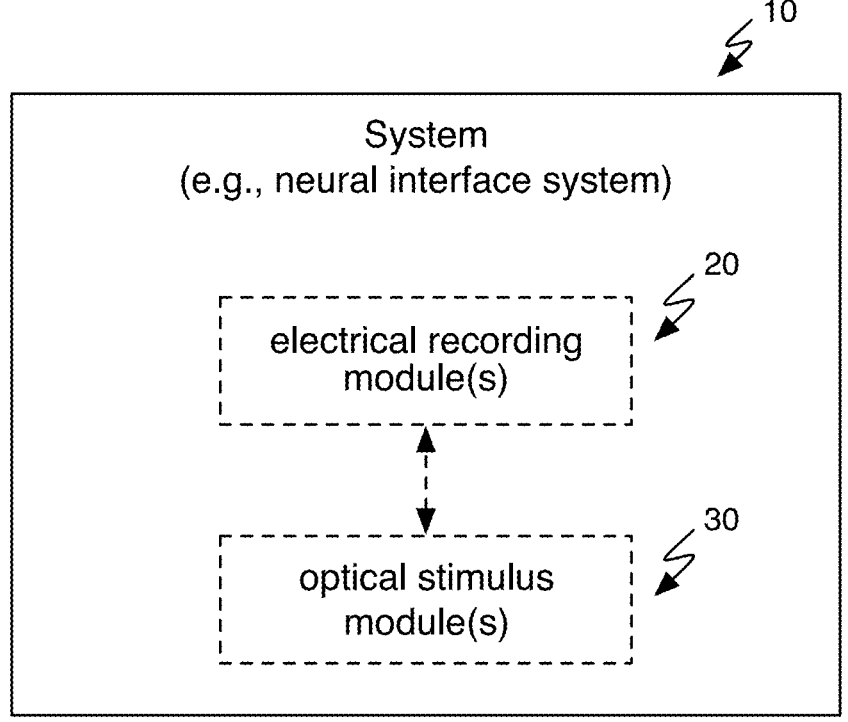
FIG. 1B is a schematic representation of a variant of the system including an electrical recording module and an optional optical stimulus module.
Figure 1C:
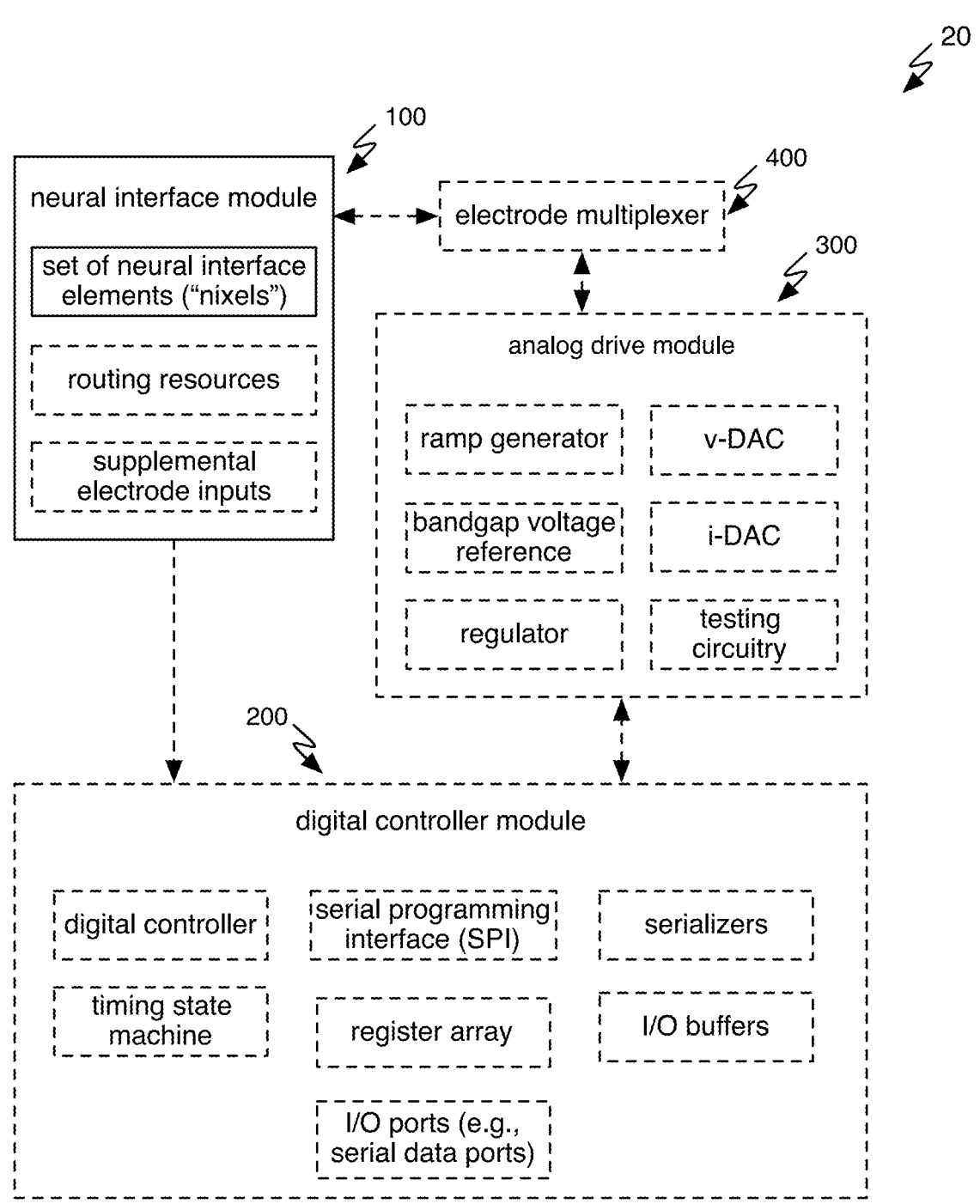
FIG. 1C is a schematic representation of a variant of the electrical recording module.

As shown in FIG. 1A, the system 10 (e.g., neural interface system) can include: a recording module 20 and/or a stimulus module 30. In an example, as shown in FIG. 1B, the system can include an electrical recording module and/or an optical stimulus module. In an example, as shown in FIG. 1C, the recording module 20 can optionally include a digital controller module 200, an analog drive module 300, an electrode multiplexer 400, and/or any other suitable components.

In variants, the system 10 (e.g., neural interface system) can function to read signals from neurons (e.g., reading electrical signals via electrodes) and/or transmit signals to neurons (e.g., transmitting electrical signals via electrodes and/or transmitting light as optical signals via LEDs). The system 10 can additionally or alternatively function to apply electrical signals to recording electrodes to determine the quality of the electrical interface by performing an impedance measurement at various frequencies and amplitude levels.

2. Examples

In an example, the system can include an electrical recording module configured to record electrical signals from a set of neurons via an array of electrodes. The system can optionally include an optical stimulus module configured to transmit light signals to the set of neurons via an array of LEDs. In a first variant the system can be an application-specific integrated circuit (ASIC). In a second variant, the system can be a probe that includes the ASIC, wherein the probe can interface with neurons in vivo and/or in vitro.

In an example, the system (e.g., an electrical recording module of the system) can include a neural interface module, a digital controller module, and an analog drive module. In a specific example, the neural interface module can be configured to measure, amplify, and digitize neural signals from a set of active electrode inputs (e.g., 512 active electrode inputs) in parallel, where each active electrode input can be an electrode (e.g., where the active electrode input interfaces with a neuron) and/or can be connected to a separate electrode (e.g., where the electrode interfaces with a neuron). In a specific example, the digital controller module can be configured to store and multiplex digitized signals to serial data outputs, generate signals (e.g., arbitrary waveforms), and/or determine settings (e.g., bias settings, timing settings, configuration settings, etc.). In a specific example, the analog drive module can be configured to generate programmable bias voltages and/or currents for the neural interface module, generate static and/or time-varying reference signals for the neural interface module, generate static and/or time-varying test signals for the neural interface module for stimulating neurons or applying electrical signals for testing and characterization purposes, and/or to perform impedance measurement on electrodes using various amplitudes and frequencies.

In an example, the neural interface module can include an array of neural recording elements ("nixels"), each configured to record a neural signal using: a pair of active electrode inputs (e.g., wherein each electrode input is coupled capacitively to an analog switch-matrix), a differential amplifier (e.g., LNA) configured to record a differential signal from the pair of active electrode inputs (e.g., using one electrode input as the reference for the other), an analog memory component (e.g., an analog sample-and-hold functioning as an analog memory) configured to store the analog differential signal, and an analog-to-digital converter component (e.g., a comparator functioning as the analog front-end of a single-slope analog-to-digital converter) configured to digitize the output from the analog memory component. The digitized code corresponding to the stored analog value can then be obtained using a global counter circuit and a dedicated digital memory component for every neural interface element (e.g., where each neural interface element has a separate digital memory component). The neural interface module can optionally include a set of passive electrode inputs (e.g., 16 passive electrode inputs, including 8 reference electrode inputs and 8 test electrode inputs) used to receive external electrical signals (e.g., acting as analog reference or test signals directly without any processing circuitry in the signal path until the neural interface element inputs). In specific examples, the analog switch matrix can be programmed to perform one or more of: changing the input polarity of the differential amplifier; disconnecting the differential amplifier input from active electrode input(s) and connecting the differential amplifier input to other signals (e.g., globally routed test or reference signals, generated on-chip and/or externally); disconnecting an active electrode input from the differential amplifier input and connecting the active electrode input to an analog drive module testing circuit to measure the impedance level seen at a given electrode input in a selected neural interface element at various frequencies and amplitude levels; and/or otherwise route signals.

The neural interface elements can optionally include spike neural interface elements and Local Field Potential (LFP) neural interface elements. In an example, spike neural interface elements can be used for neural spike recording applications, and LFP neural interface elements can be used for neural LFP signal recording applications. In a specific example, spike and LFP neural interface elements can have the same integrated recording electronics (e.g., differential amplifier, sample-and-hold, comparator, etc.), but can be operated using different gain settings, low-pass corner frequency settings, and/or high-pass corner frequency settings for the respective differential amplifiers.

The system can optionally be configured to operate in one or more modes, such as: a fully differential mode, a single-ended mode, a test mode, and/or a stimulus mode. In an example, the routing resources can be used to switch between operating modes of the system and/or a component therein. For example, the system can be configured to operate in one or more modes, such as: a fully differential mode, a single-ended mode, a test mode, and/or a stimulus mode. In a first example, the system 10 operating in a fully differential mode can record a differential signal from two electrodes using a neural recording element (e.g., where one electrode in the pair of electrodes acts as a reference for the other electrode). In a second example, the system operating in a single-ended mode can record a signal from a single electrode using a neural recording element (e.g., wherein a global passive electrode or on-chip generated reference signal is used as the reference). In a third example, the system 10 operating in a test mode can apply test signals to the electrodes (e.g., to characterize the electrode interface in terms of impedance levels at various frequencies and amplitude levels or to characterize frequency response of the recording channels from input to the output in terms input/output amplitudes and corner frequencies of the signal path). In a specific example, in the test mode, the neural interface module 100 can be configured to amplify and digitize the test signal using the main recording signal path of the neural interface module (e.g., from the differential amplifier to digital data ports); additionally or alternatively, the neural interface module can route the test signal to an analog test output using an integrated analog multiplexer. In a fourth example, the system operating in a stimulus mode can deliver signals to neurons (e.g., for stimulating the neurons, to measure impedance, etc.). In a specific example, a stimulus signal generated by a programmable voltage-output DAC (v-DAC) of the analog drive module can be applied to an individual active electrode input of a neural interface element via an internal coupling capacitor in the neural interface element. The resulting signal at the electrode input can optionally be recorded digitally (e.g., by the main recording signal path of the neural interface module), and/or be routed back to analog test outputs (e.g., to calibrate impedance measurement circuits).

3. Technical Advantages

Variants of the technology can confer one or more advantages over conventional technologies.

Variants of the technology can include an array of programmable unit cells (neural interface elements) used to amplify and digitize neural signals.

First, the unit cells can be used to amplify and digitize weak neural signals as early as possible in the signal path (e.g., as close to the electrode inputs as possible). At system level, this can minimize noise coupling in sensitive electrode inputs, allowing building low-noise neural systems.

Second, the use of unit cells in signal amplification and digitization can allow easier scaling of the electrode count, as all the long-distance signal routing can be done in the digital domain. This can, in turn, help to reduce the overall system noise and makes overall signal routing and power delivery easier.

Third, using programmable unit cells in a two-dimensional array structure can make overall programming, testing, and top-level signal and power routing more predictable. For example, electrode connections can be arranged right on top of each unit cell, without using any form of routing at the top redistribution layers. This can confine all routing-related parasitic effects within the cell, making the design closure easier with respect to capacitive loading and/or coupling effects.

Fourth, a uniform array structure can make routing of power, analog signals, and digital signals predictable. For example, solving these routing challenges at the unit-cell level can enable the creation of valuable routing resources within the array. These routing resources can enable the entire 2-D array to have a rich set of operational and test features. For example, the routing resources can enable the use of analog and digital signals to be routed in a mesh network across the array of cells (e.g., without any congestion).

Fifth, in variants, a uniform array structure can result in uniform pad or bumps, simplifying the power and input-and-output (I/O) routing easier at system level. In this case, analog power pads/bumps are located at the bottom of the chip and digital power and I/O pads/ bumps are located on the top of the chip, which simplifies separating analog and digital signal and power traces at system level, improving the noise performance of the system. In a specific example, leaving the core of the array for only electrode connections eliminates system noise coupling on the sensitive electrode inputs.

Sixth, a 2D array structure can enable "panel-based readout," where a panel is a portion of the readout circuit assigned to a small number of adjacent columns in the 2D array. This 2D array structure can confine the interconnectivity to a smaller area in the digital controller module, simplifying placement and routing of digital gates, enabling an easy closure in routing and timing during the physical implementation of the digital controller module. In a specific example, at system level, using panel-based readout allows building systems with lower number of electrodes with reduced power and system noise, as unused panels can be programmed to be turned off both in terms of analog and digital functions.

Seventh, variants of the technology can have testing circuits integrated at the input electrode level in a uniform fashion for all of the recording channels, allowing for testing and characterization of any recording channel on the fly (e.g., in the field). For example, combining the integrated testing circuits with panel-based readout can make the overall performance of these test inputs more uniform across the entire array.

Eighth, variants of the technology can include sophisticated analog front-end routing resources, which can enable driving the selected channel inputs with on-chip synthesized analog waveforms to characterize the complete mixed-signal data path from the electrode input to the digital outputs.

Ninth, integrating the analog front-end of an analog-to-digital converter within a unit cell can make the overall architecture suitable for modern CMOS technologies used for memory or image sensor applications, both of which heavily make use of arrayed structures. For example, the array of unit cells can benefit from industry wide manufacturing and assembly resources, developed for entirely different applications.

Tenth, variants of the technology can use on-chip generated common references instead of an external reference. Conventional recording methods use single-ended electrode inputs to read signals from neurons. These single-ended electrode inputs typically use a pseudo-differential architecture, where the single-ended electrode input is amplified and digitized with respect to a shared reference input. However, in this conventional method, the source and/or loading of the reference input is not the same as the active electrode input. Therefore, in a specific example, the noise sources are not correlated at the source, and the noise can be quite different between the reference electrode input and the active electrode input when the signals are received at an amplifier (e.g., due to different bandwidths associated with each signal path). Since reference inputs are usually heavily loaded compared to other inputs, high-frequency system noise cannot be suppressed effectively. In some cases, it can also be possible to suppress the common-mode system noise coupled to active and reference inputs by digitizing the reference signals through regular active recording channels and subtracting digitized reference signal from digitized active electrode signals. To reduce saturation due to possibly high common mode signal levels, in a specific example, using lower gain may be required. In some cases using this method can result in lower system noise, especially when it becomes matching the loading at the reference channels and active electrode inputs. Using panel based recording can optionally help to solve this issue as it can limit the loading of the reference inputs due to using smaller in a specific example, elements. Furthermore, using dedicated reference and test inputs per panel can also reduce the effective loading of the reference inputs.

Eleventh, in variants, to achieve an optimal signal-to-noise ratio, one would need the neural signal and the reference to come from the same type of cell or medium. Variants of the technology can implement a fully differential low-noise amplifier at the input stage; this assumes that only one active pulse will come from one of these inputs, while the other idle input can act as a reference, suppressing any common system noise on these signals. In an example, the true differential reading capability of the input circuits can differentiate the source of the input pulse because the polarity of the readout signal can indicate the source of the active channel. In a specific example, collisions where a neural signal pulse from each input arrives at approximately the same time (which would reduce the detected signal level) can be ignored as long as the rate of collusion occurrence is not too high. Assuming this collision rate is low, using true differential operation can improve the signal-to-noise ratio and all electrode inputs in the unit cells (the neural recording elements) can contribute to signal recording. For example, if there are 256 differential neural recording electrode inputs, then 512 electrode inputs can be used for recording (e.g., where any or all of the electrode inputs can carry useful neural spike information). In variants, in the event that the collision rate is considerably high, the system can optionally be configured to operate in a pseudo differential mode (e.g., single-ended mode). In that case, the user can use one of the differential electrode inputs for neural recording, and use global reference inputs for pseudo differential mode. Since every neural recording element has 2 electrode inputs, one of them can either be not utilized, or the system can use these electrode inputs in a time interleaved fashion after a certain number of consecutive recordings.

Twelfth, variants of the technology can reduce noise in the recorded neural signals by integrating an analog-to-digital component (e.g., a comparator functioning as the analog front-end of a single-slope analog-to-digital converter) into each unit cell (neural interface element). In variants, the integrated analog-to-digital component can enable multiplexing of recorded neural signals in digital format after digitization, which can reduce noise in the recorded output signals.

Thirteenth, variants of the technology can include an active probe for in vitro and/or in vivo neural engineering (e.g., for electrocorticography (ECoG) experiments). The active probe can include a probe head featuring electrodes and/or LEDs. In a first example, the probe can be a unidirectional probe functioning to read from the set of neurons (e.g., recording electrical signals). In a second example, the probe can be a bidirectional probe functioning to read from and write to the set of neurons (e.g., recording electrical signals and transmitting light signals). The probe can optionally have a modified geometry and/or flexibility based on the type of experiment. For example, the probe can be flexible and longer (e.g., at least 100 mm) when the probe head is implanted in vivo in a brain. In another example, the probe can be rigid and shorter (e.g., less than 100 mm) when the probe is used for in vitro experiments. In a specific example, the probe can include a cell container (e.g., a cell well) on top of the probe head, wherein neurons can be cultured in the cell container for in vitro experimentation.

Fourteenth, variants of the technology when compared to single ended recording systems, can use half of the recording channels to record a given number of input electrodes, which can reduce the power dissipation and/or can reduce the system noise by reducing the switching noise and/or reducing the system clock frequency of the chip due to the reduced number of parallel working recording channels.

However, further advantages can be provided by the system and method disclosed herein.

4. System

As shown in FIG. 1A, the system 10 (e.g., a neural interface system) can include one or more recording modules 20 and/or one or more stimulus modules 30. As shown in FIG. 1B, an example of the system 10 can include an electrical recording module and/or an optical stimulus module. However, the system can additionally or alternatively include other components. In variants, the system 10 can function to read signals from neurons (e.g., reading electrical signals via electrodes) and/or transmit signals to neurons (e.g., transmitting electrical signals via electrodes and/or transmitting light signals via LEDs). The system 10 can additionally or alternatively function to apply electrical signals to recording electrodes to determine the quality of the electrical interface by performing an impedance measurement at various frequencies and amplitude levels. The system can optionally be used for electrocorticography (ECoG).

The system preferably interfaces with neurons, but can additionally or alternatively interface with other cells (e.g., retinal cells, any other somatic cells, reproductive cells, stem cells, plant cells, etc.) and/or any other signal source. The neurons can be in vivo (e.g., within a brain), ex vivo, in vitro, and/or otherwise configured. The neurons can be derived from a human, any other mammal (e.g., chimpanzee, rat, rabbit, mouse, etc.), and/or any other animal. In a specific example, when the neurons are in vivo, all or a portion of the system (e.g., the head of the probe) can be implanted within the brain of an organism or on the surface of the brain of an organism. The organism can be a human, any other mammal (e.g., chimpanzee, rat, rabbit, mouse, etc.), and/or any other animal.

The neurons can optionally be optogenetically modified. In an example, neurons can be genetically modified by transfecting the cells with a light-sensitive protein (e.g., using a virus with a plasmid and capsid) that acts as an optogenetic actuator (e.g., optogenetic effector). In a specific example, optogenetic actuators can produce a biochemical signal (e.g., an action potential) in response to receiving light at a specific wavelength. The capsid can be an adeno-associated virus capsid (e.g., AAV2.7M8) and/or any other suitable capsid. The plasmid can be an opsin, a fluorescent biosensor protein, and/or any other suitable plasmid. Opsin examples include: CheRiff, ChroMD, ChroME, ChroME2S, ChRmine (e.g., ChRmine-mScarlet), ChrimsonR (e.g., including red-shifted variants), ReachR, and/or any other opsin. In an illustrative example, the cells can be transfected using: AAV2.7m8 hSyn1-ChRmine-Kv2.1-WPRE. Fluorescent biosensor protein examples include: GCaMP8s, GCaMP8m, jRGecola, YCaMP, iGECI, and/or any other suitable protein. The opsin can be activated by blue light, green light, red light, and/or any other wavelength.

The system 10 can include one or more recording modules 20 (e.g., electrical recording modules), which functions to record electrical signals from a set of neurons. Additionally or alternatively, the recording module 20 can function to transmit electrical signals from the set of neurons. As shown in FIG. 1C, the electrical recording module can include a neural interface module 100. The recording module 20 can optionally include a digital controller module 200, an analog drive module 300, an electrode multiplexer 400, and/or any other suitable components. In an example, the recording module 20 (e.g., electrical recording module) can include: a set of electrodes (e.g., an array of electrodes) and an IC (e.g., an electrical recording IC).

Figure 7A:
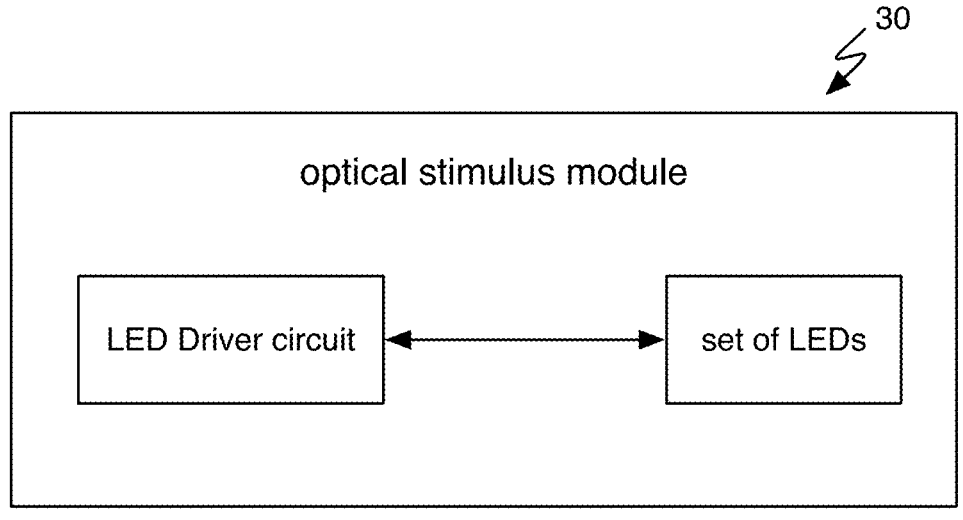
FIG. 7A depicts a schematic representation of an example of an optical stimulus module.

The system 10 can optionally include an optical stimulus module 30 (or multiple optical stim, which functions to transmit light signals to a set of neurons. An example is shown in FIG. 7A. In an example, the optical stimulus module 30 can include: a set of LEDs (e.g., an array of LEDs) and an IC (e.g., an LED driver IC). The material of the set of LEDs can include indium gallium nitride, gallium nitride (e.g., biocompatible gallium nitride), indium gallium phosphide, an organic emitter, and/or any other light emission materials. The wavelength of the set of LEDs can be between 300 nm-900 nm or any range or value therebetween (e.g., 510 nm-550 nm, approximately 530 nm, 450 nm-485 nm, 500 nm-570 nm, 625 nm-750 nm, etc.). In examples, the LED irradiance at 10 μm is between 0.01 mW/cm$^2$-100 mW/cm$^2$ or any range or value therebetween (e.g., less than 5 mW/mm$^2$, less than 2.5 mW/mm$^2$, etc.). The IC of the stimulus module 30 (e.g., optical stimulus module) can function to drive the set of LEDs. For example, the IC can include a passive driver. In a first example, the IC can iterate through each row of LEDs in the set of LEDs (e.g., in a grid of LEDs), controlling all or a subset of LEDs in the row to turn on (e.g., the maximum number of LEDs simultaneously illuminated is the number of LEDs in a row). In a second example, each LED can be driven independently by the IC. The stimulus module 30 can optionally include one or more microoptics components, which can function to collimate light, homogenize light, focus light (e.g., onto a smaller number of cells), and/or otherwise modify light emitting from the stimulus module 30. Examples of microoptics components can include: lenses (e.g., microlens, diffractive lens, metalens, etc.), back reflectors, a modified LED shape, waveguides, a spacing gap, a combination thereof, and/or any other optics components.

Figure 3:
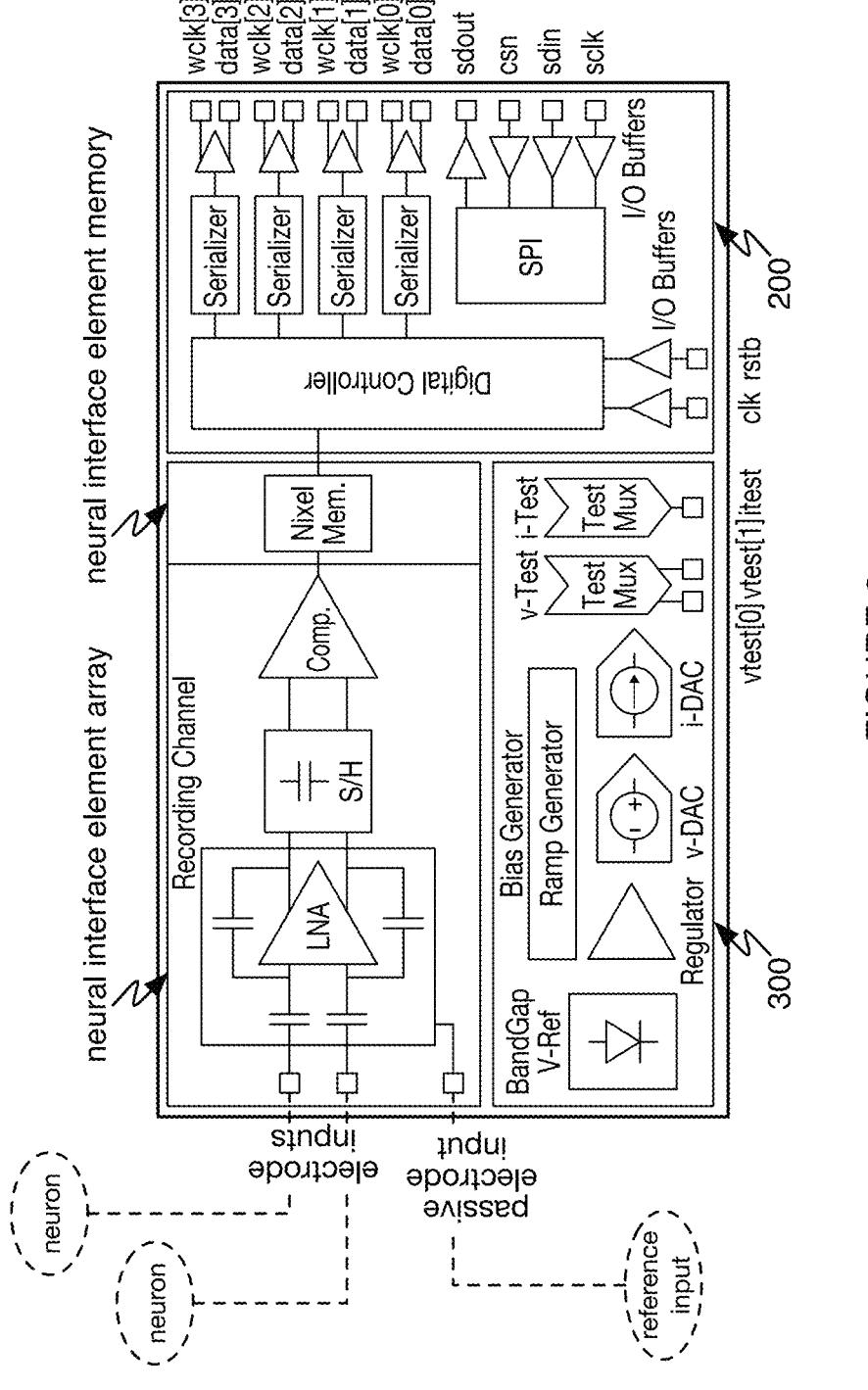
FIG. 3 depicts an example of the system.
Figure 5A:
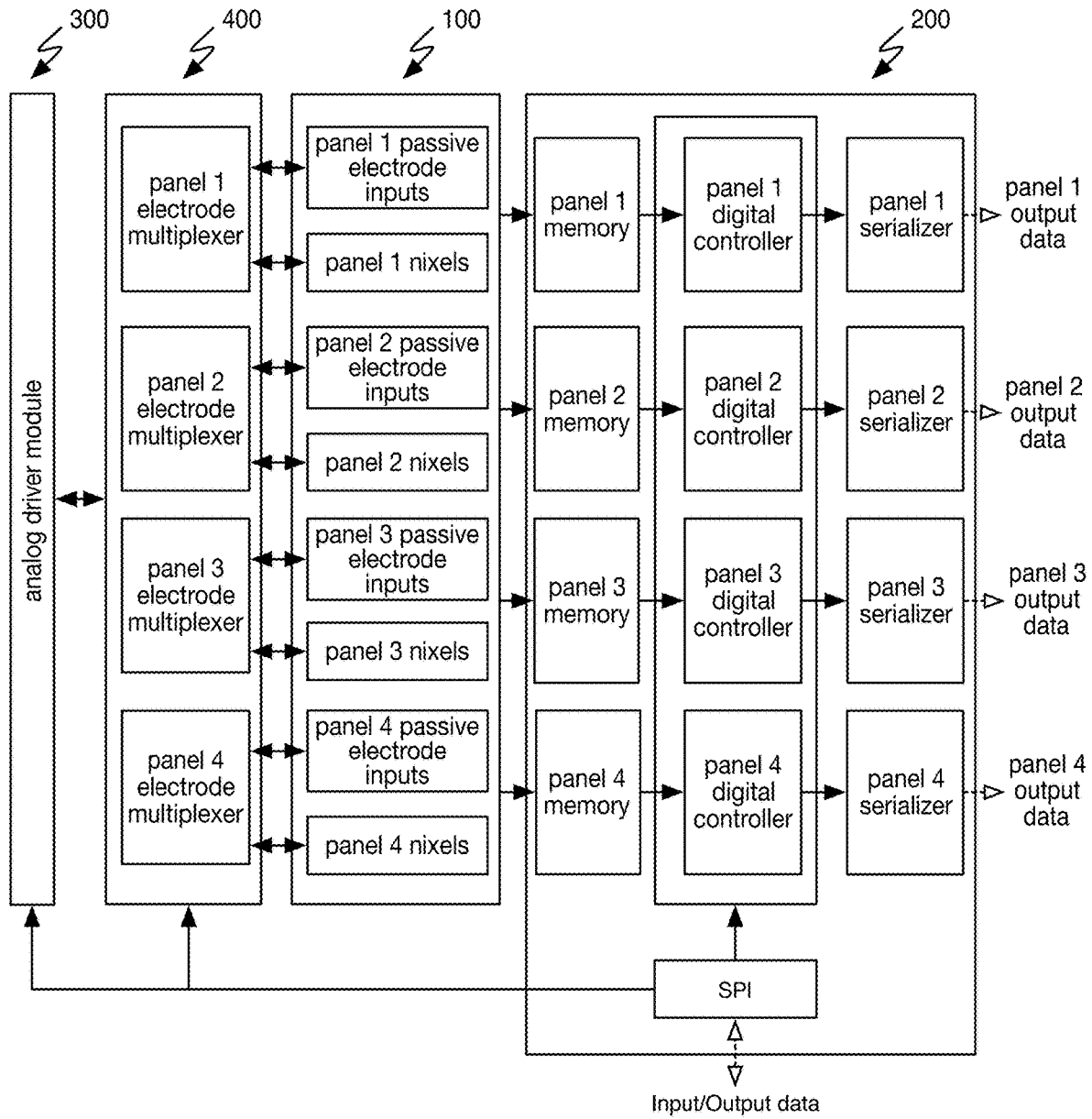
FIG. 5A depicts an example of the system, including four panels.

In variants, the system 10 can be or include an integrated circuit (IC) (e.g., an application-specific integrated circuit (ASIC)). For example, the system 10 can be or include an IC that includes the neural interface module 100, the digital controller module 200, analog drive module 300, and/or any other system components. Examples are shown in FIG. 3 and FIG. 5A. The system can additionally or alternatively include a set of ICs (e.g., where all or a portion of the neural interface module 100, digital controller module 200, analog drive module 300, and/or any other system components are distributed across the set), any other computing system, and/or any other system. All or a subset of the system components can optionally be manufactured together. For example, the neural interface module 100, digital controller module 200, and analog drive module 300 are preferably manufactured together, but can alternatively be separately manufactured and connected.

Figure 7B:
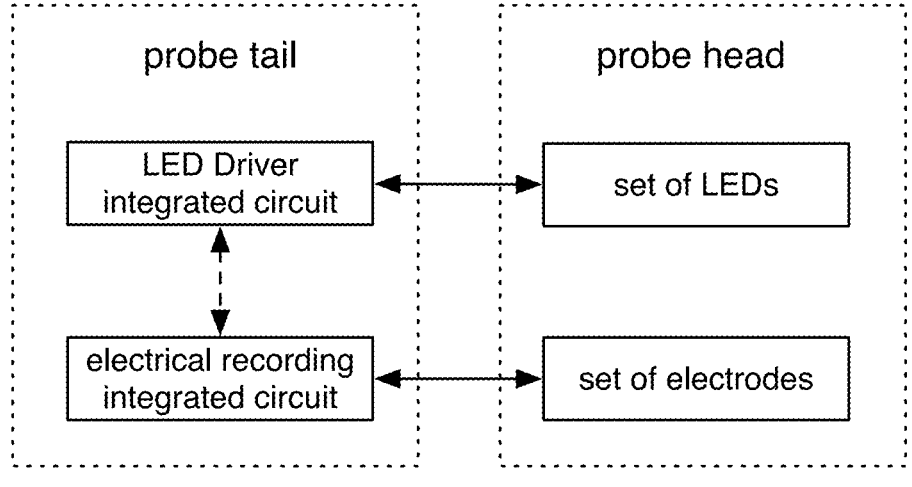
FIG. 7B depicts a schematic representation of an example of the system (e.g., a probe), including an electrical recording module and optical stimulus module.
Figure 9A:
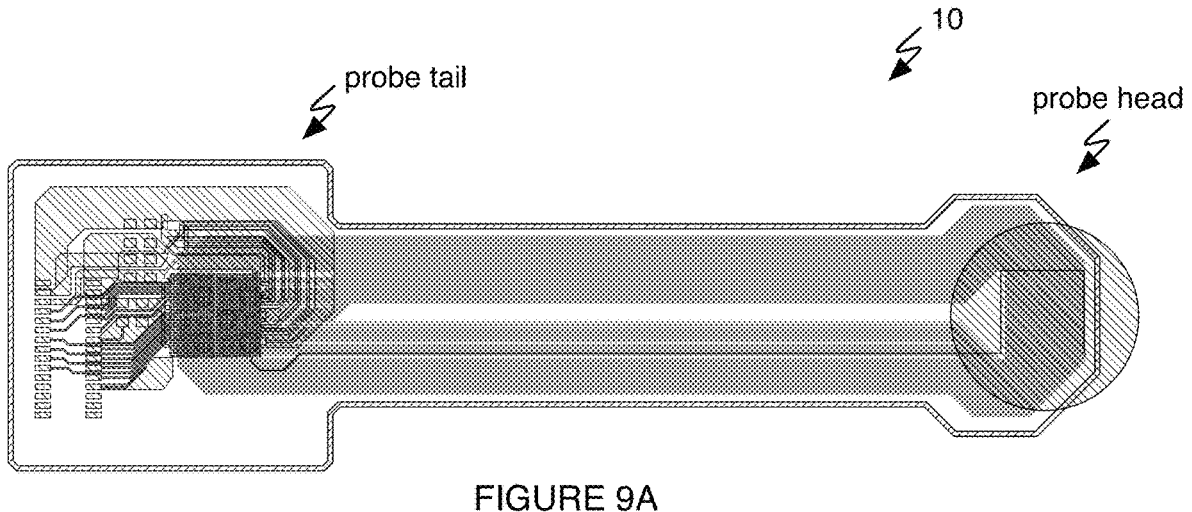
FIG. 9A depicts a first example of the system (e.g., an in vivo probe), including an electrical recording module.
Figure 9B:
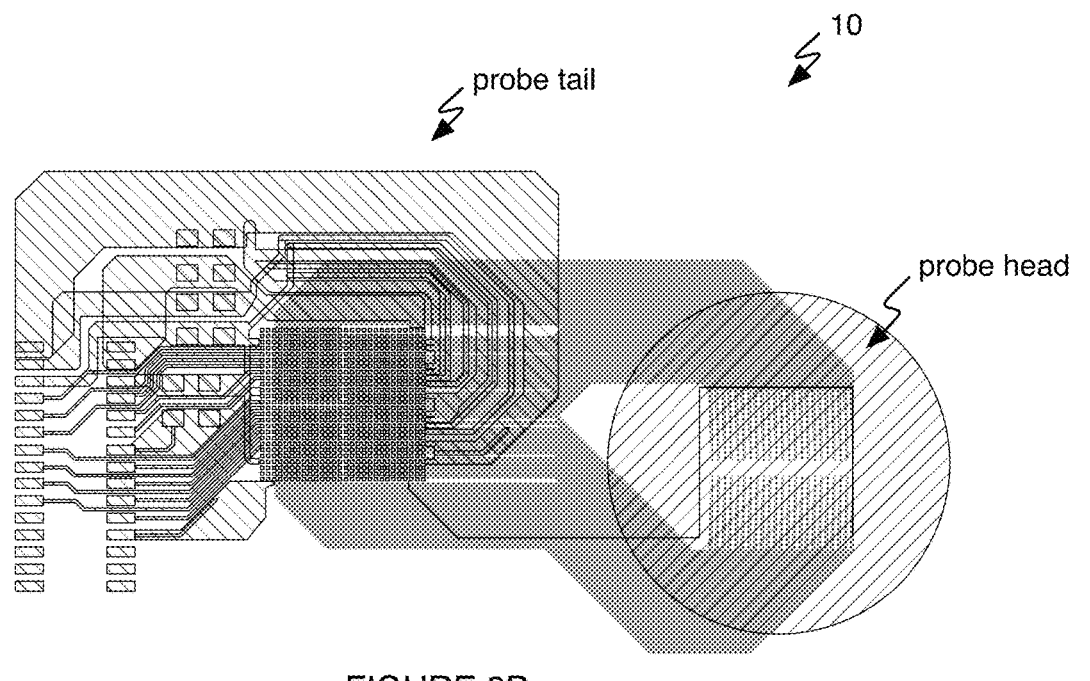
FIG. 9B depicts a second example of the system (e.g., an in vitro probe), including an electrical recording module.
Figure 9C:
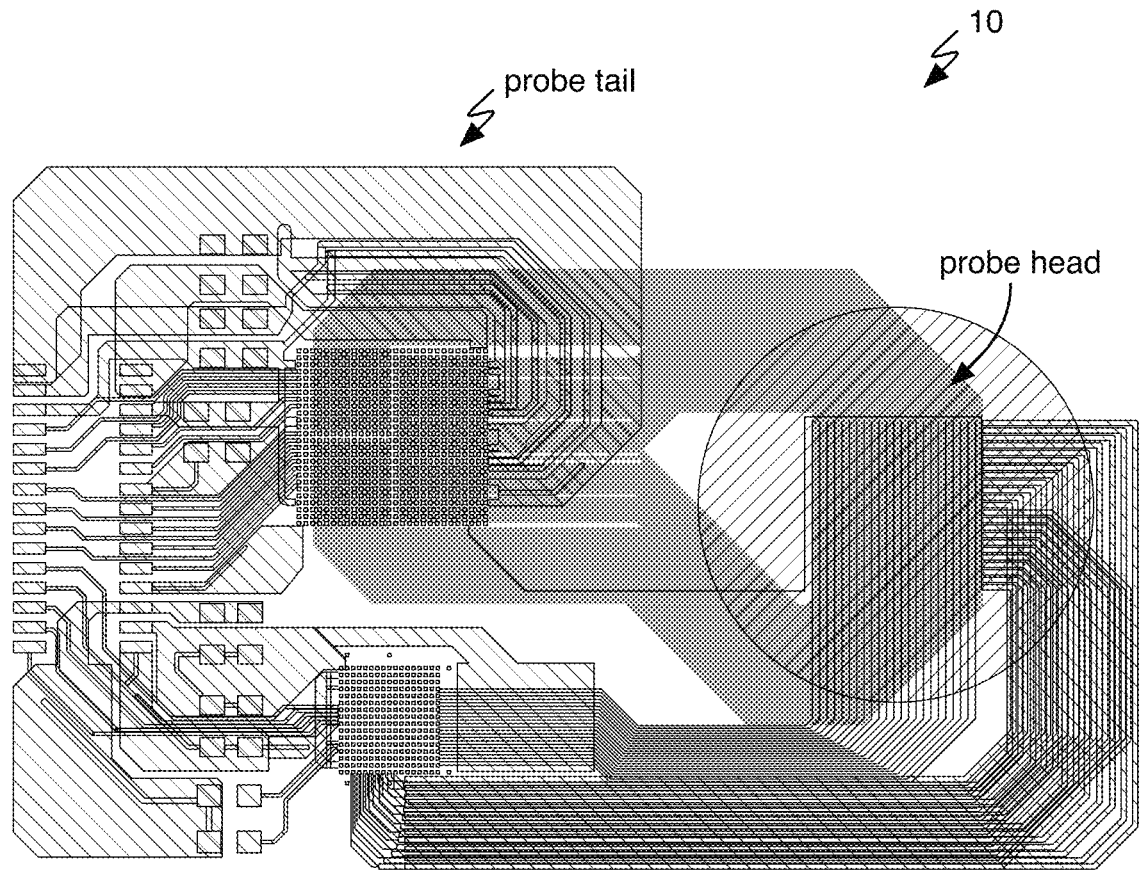
FIG. 9C depicts a third example of the system (e.g., an in vitro probe), including an electrical recording module and an optical stimulus module.
Figure 10A:
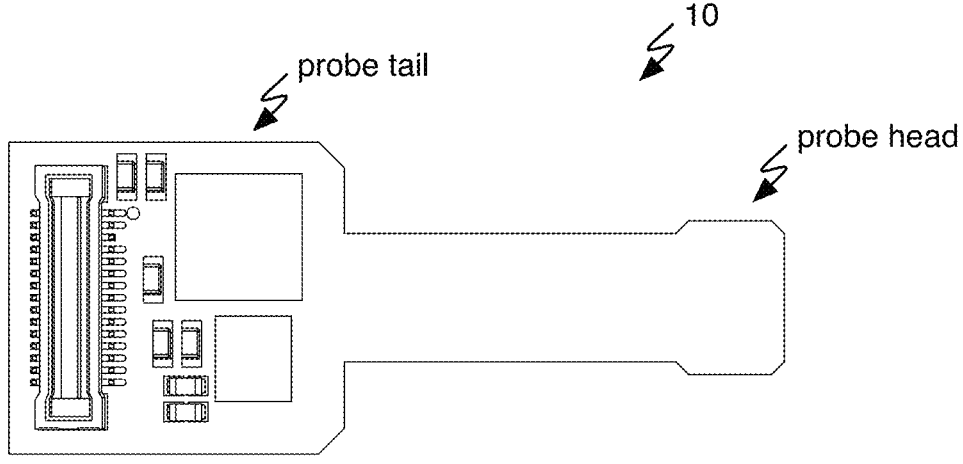
FIGS. 10A-10B depict specific examples of the system.
Figure 10B:
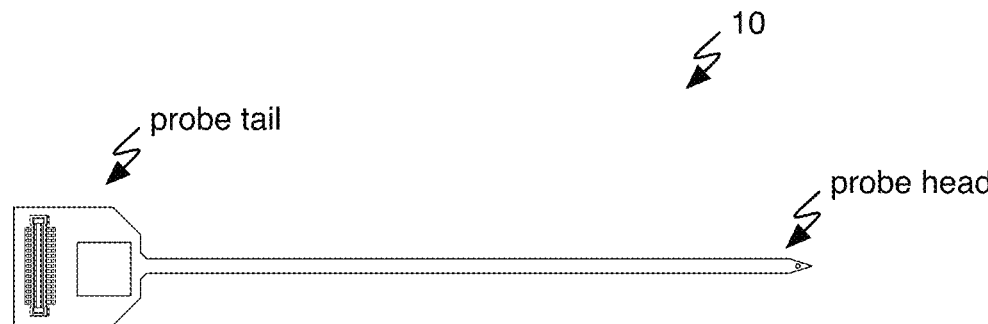

In a first embodiment, the system 10 can be an IC (e.g., an ASIC). In a first example of the first embodiment, the IC includes on-chip electrode inputs (e.g., electrode inputs functioning as electrodes), wherein the IC directly interfaces with a set of neurons. In a second example of the first embodiment, the IC is connected to separate electrodes, wherein the separate electrodes interface with a set of neurons. In a second embodiment, the system can be a probe that includes the IC (e.g., at a tail of the probe) and a set of electrodes (e.g., at a head of the probe), wherein the set of electrodes can interface with a set of neurons (e.g., in vivo and/or in vitro). The probe can optionally also include a set of LEDs (e.g., μLEDs) (e.g., at the head of the probe). An example is shown in FIG. 7B. In a first example, the probe can be a unidirectional probe functioning to read from the set of neurons (e.g., recording electrical signals). Specific examples are shown in FIG. 9A and FIG. 9B. In a second example, the probe can be a bidirectional probe functioning to read from and write to the set of neurons (e.g., recording electrical signals and transmitting light signals and/or electrical signals). A specific example is shown in FIG. 9C.

In an example of the second variant, the probe can include a substrate (e.g., a rigid substrate or a flexible substrate), wherein one or more ICs are located at a first end of the substrate (e.g., the probe tail), and the set of electrodes and the optional set of LEDs are located at a second end of the substrate (e.g., the probe head). Examples are shown in FIG. 9A, FIG. 9B, FIG. 9C, FIG. 10A, FIG. 10B, FIG. 11A, FIG. 11B, and FIG. 11C. In an example, a set of wires (e.g., on the substrate) can connect the set of electrodes and/or the set of LEDs to the one or more ICs. The distance between the first end of the substrate and the second end of the substrate can optionally be between 0 mm-500 mm or any range or value therebetween (e.g., at least 10 mm, at least 20 mm, at least 50 mm, at least 100 mm, at least 200 mm, etc.). In a specific example, a probe used in vivo (e.g., where the probe head is implanted in or on the brain) can have a distance between the first end of the substrate and the second end of the substrate that is greater than a threshold (e.g., at least 50 mm, at least 100 mm, at least 200 mm, at least 500 mm, etc.).

In an example, the set of electrodes can be connected to a first IC (e.g., a electrical recording IC configured to record electrical signals), and the set of LEDs can be connected to a second IC (e.g., an LED driver IC configured to drive the set of LEDs to transmit light signals). For example, each electrode in the set of electrodes can be connected to a corresponding electrode input in the electrical recording IC (e.g., each electrode is connected to an electrode input of a neural interface element on the IC). In a specific example, the set of electrodes can include one or more pairs of electrodes, wherein each pair of electrodes is connected to a pair of electrode inputs at the electrical recording IC (e.g., a first electrode in a pair of electrodes is connected to a first electrode in a pair of electrode inputs, and a second electrode in the pair of electrodes is connected to a second electrode in the pair of electrode inputs).

Figures 11A, 11B, 11C:
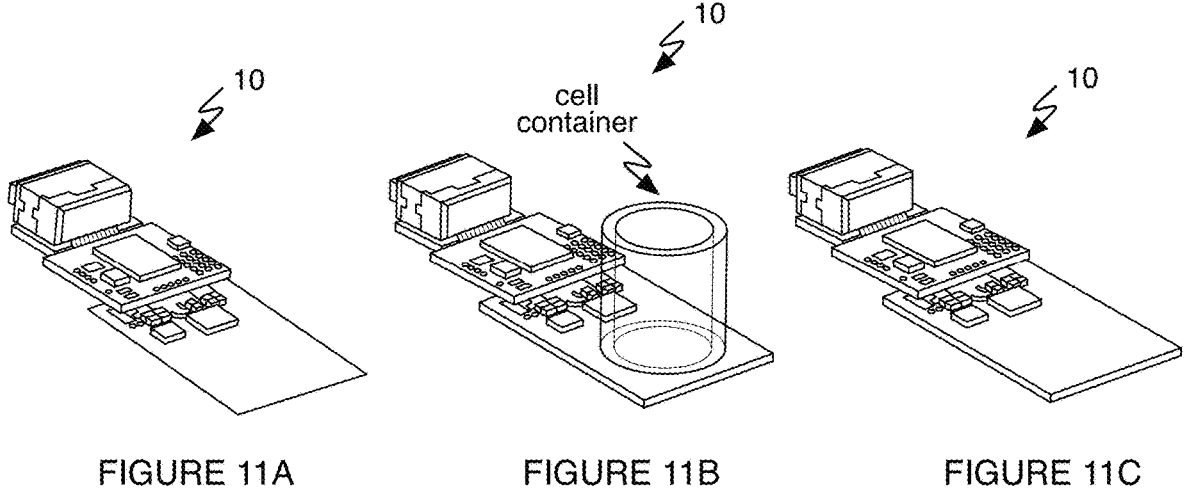
FIG. 11A depicts a first illustrative example of the system, including a flexible backing.
FIG. 11B depicts a second illustrative example of the system, including a rigid backing and a cell container.
FIG. 11C depicts a third illustrative example of the system, including a rigid backing.

The substrate can be rigid or flexible. An example of a probe with a flexible substrate is shown in FIG. 11A. Examples of probes with rigid substrates are shown in FIG. 11B and FIG. 11C. The substrate can optionally include one or more layers of polyimide and/or one or more layers of metal. Manufacturing a flexible substrate can optionally include using a laser lift off method and/or a water release method to release the flexible substrate (e.g., including one or more layers of polyimide) from one or more layers of metal. In a first example, a probe used in vitro can include a rigid substrate. In a specific example, the probe can include a cell container (e.g., a glass container arranged on top of the probe head), wherein the set of neurons can be cultured in the cell container (e.g., while interfacing with the set of electrodes and/or the set of LEDs). An example is shown in FIG. 11B. In a second example, a probe used in vivo (e.g., where the probe head is implanted in or on a brain) can include a flexible substrate.

Figure 8:
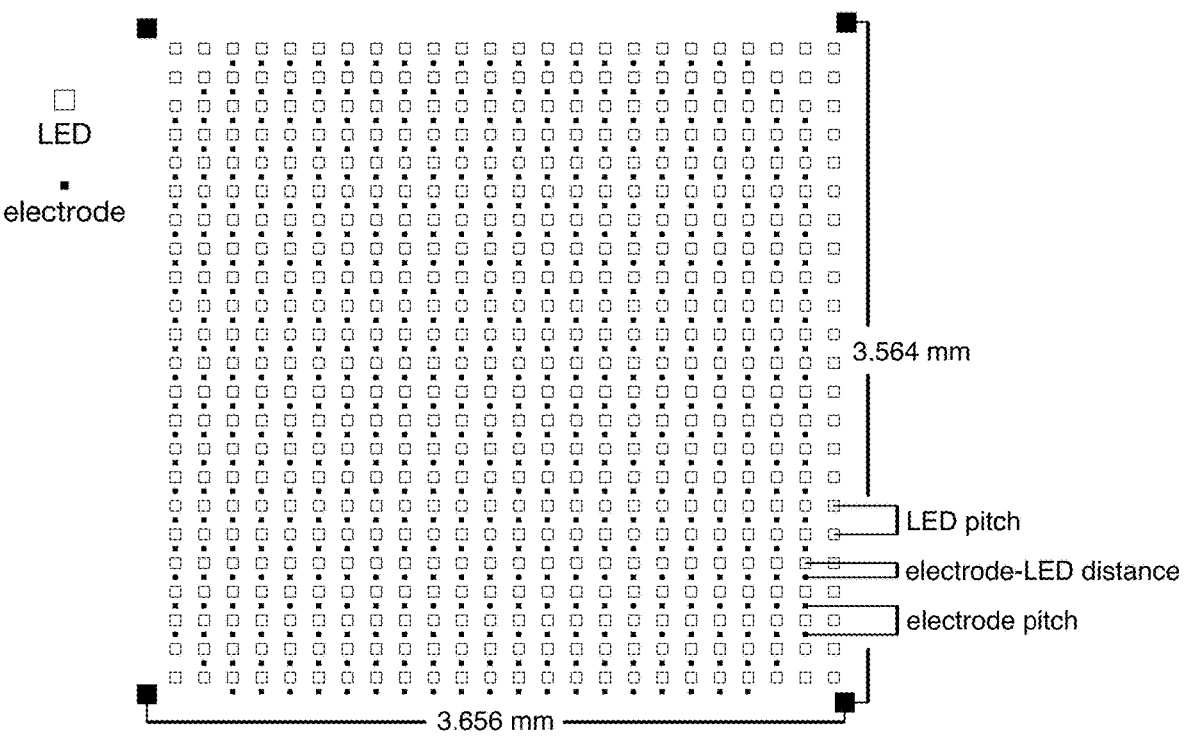
FIG. 8 depicts a specific example of a probe head, including a set of LEDs and a set of electrodes

In an example, the probe (e.g., the head of the probe) can include an array of electrodes and/or an array of LEDs. In a specific example, the array of electrodes can be arranged in a grid (e.g., a 2D grid). In another specific example, the array of LEDs can be arranged in a grid (e.g., a 2D grid). When the probe includes an array of electrodes and an array of LEDs, the array of electrodes (e.g., grid of electrodes) and the array of LEDs (e.g., grid of LEDs) can optionally be partially or fully overlapping. In a specific example, the array of electrodes and the array of LEDs can be staggered (e.g., such that individual electrodes do not overlap with individual LEDs). The array of electrodes can optionally occupy an area between 5 mm²-100 mm² or any range or value therebetween (e.g., at least 10 mm², approximately 13 mm², etc.). The number of electrodes in the array of electrodes can optionally be between 100-100,000 or any range or value therebetween (e.g., 512, at least 200, at least 256, at least 400, at least 500, etc.). The array of LEDs can optionally occupy an area between 5 mm²-100 mm² or any range or value therebetween (e.g., at least 10 mm², approximately 13 mm², etc.). The number of LEDs in the array of LEDs can optionally be between 100-100,000 or any range or value therebetween (e.g., 512, at least 200, at least 256, at least 400, at least 500, etc.). The number of LEDs is preferably within a threshold of the number of electrodes (e.g., within 100, within 50, within 20, etc.), but can alternatively not be within a threshold. The pitch of the array of electrodes (e.g., the distance between adjacent electrodes) can optionally be between 50 μm-500 μm or any range or value therebetween (e.g., 100 μm-200 μm, approximately 150 μm, etc.). In a specific example, having an electrode array pitch of at least 50 μm can ensure two adjacent electrodes do not receive a signal from the same neuron. In another specific example, having an electrode array pitch of less than 500 μm can ensure two adjacent electrodes receive similar noise (e.g., which is then canceled out during differential recording). The pitch of the array of LEDs (e.g., the distance between adjacent LEDs) can optionally be between 50 μm-500 μm or any range or value therebetween (e.g., 100 μm-200 μm, approximately 150 μm, etc.). In an overlapping portion of the array of electrodes and the array of LEDs, the distance between an LED and an adjacent electrode can be between 25 μm-500 μm or any range or value therebetween (e.g., 25 μm-100 μm, 50 μm-100 μm, approximately 75 μm, etc.). A specific example is shown in FIG. 8. In an illustrative example, an LED in the array of LEDs transmits a light signal to a neuron and an electrode adjacent to the LED receives an electrical signal from the neuron.

The system can optionally include or interface with a computing system. In an example, the digital controller module 200 can transmit data (e.g., recorded neural signals) to the computing system. The computing system can include one or more: CPUs, GPUs, TPUs, custom FPGA/ASICS, microprocessors, servers, cloud computing, and/or any other suitable components. The computing system can be local, remote (e.g., cloud computing server, etc.), distributed, and/or otherwise arranged relative to any other system or module.

The system can optionally interface with one or more supplementary devices. Examples of supplementary devices include: measurement devices (e.g., temperature sensor, current sense resistors, pressure sensor, chemical sensor, humidity sensor, multimeter, etc.), telemetry components, user interfaces, computing systems, and/or any other devices. In a specific example, measurement components can measure supply current and/or power dissipation. In another specific example, telemetry components can send data (e.g., measurement data, neural signals, etc.) to a remote system. The supplementary devices can optionally transmit data (e.g., signals) to one or more components of the system (e.g., to the digital controller module 200, to the neural interface module 100, etc.). Examples of data include: measurements, user inputs, test signals, and/or any other data.

4.1. Neural Interface Module 100

The neural interface module 100 (e.g., interface module) preferably functions to interface with a set of neurons, including receiving signal pulses from neurons and/or applying inputs (e.g., test inputs) to electrodes. The neural interface module 100 can be connected to the analog drive module 300, the digital controller module 200, and/or any other system components. The neural interface module 100 preferably interfaces (directly or indirectly) with neurons, but can additionally or alternatively interface with any other signal source.

The neural interface module 100 can include a set of neural interface elements ("nixels") and routing resources. The neural interface module 100 can optionally include a set of passive electrode inputs, other integrated circuit components, and/or any other suitable components.

Figure 6:
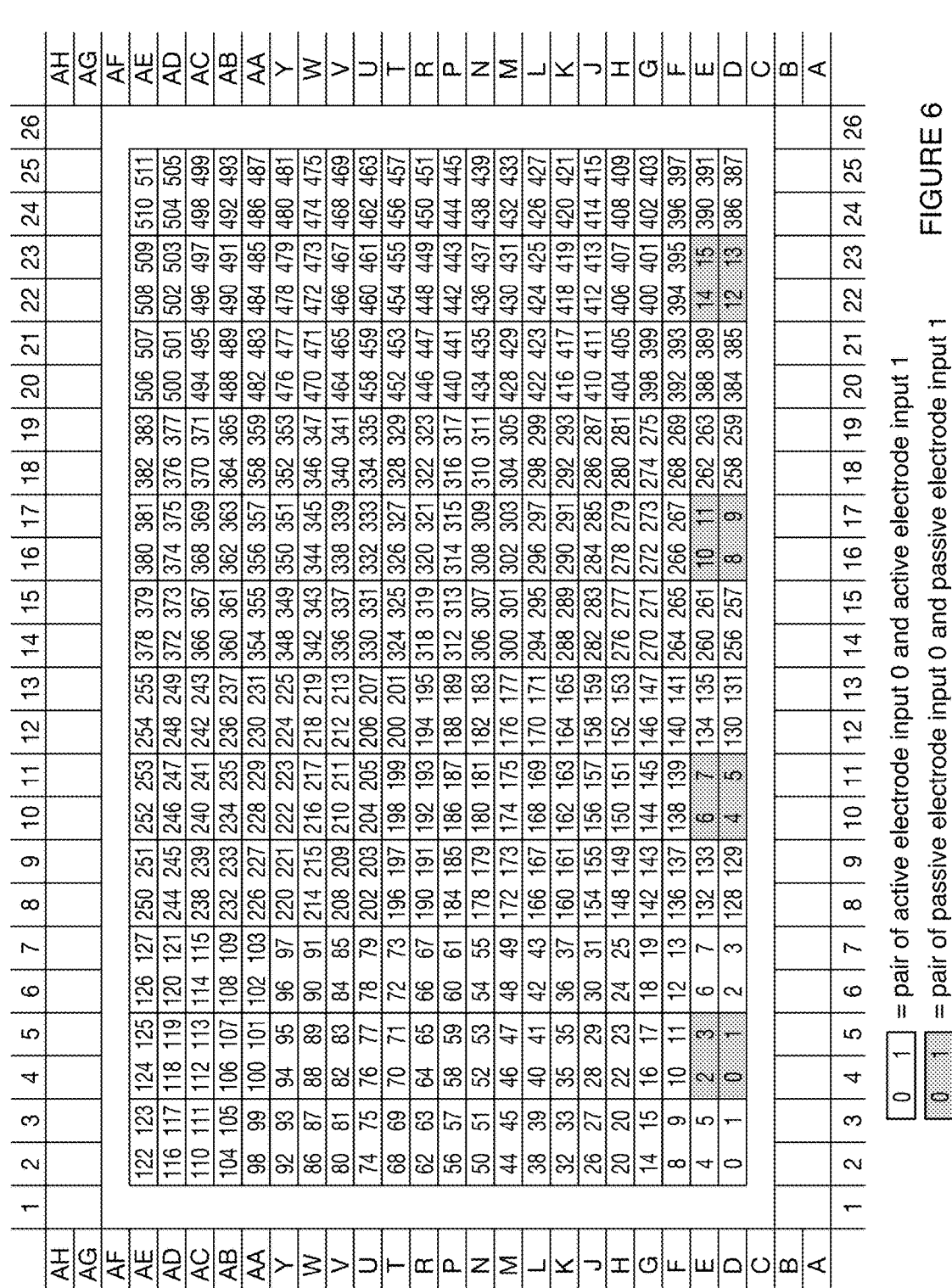
FIG. 6 depicts an example of an electrode mapping of the system (e.g., looking from the bump side), including active electrode inputs and passive electrode inputs. In a specific example, a subset of the passive electrode inputs (e.g., the passive electrode inputs: [0,1], [4,5], [8,9], and [12,13]) are designated as an external reference electrode inputs (e.g., wherein each pair of external reference electrode inputs corresponds to a panel), and another subset of the passive electrode inputs (e.g., the passive electrode inputs: [2,3], [6,7], [10,11], and [14,15]) are designated as external test electrode inputs.

The number of neural interface elements in the neural interface module 100 can range from one single element (1) to 1 million elements or any range or value therebetween (e.g., at least 2, at least 10, at least 50, at least 100, at least 200, at least 256, at least 5000, at least 10000, 64, 128, 256, 512, etc.), but can alternatively be greater than 1 million elements. The set of neural interface elements are preferably arranged in a 2D array (e.g., a grid), but can alternatively be arranged in a 1D array, a 3D array (e.g., stacked 2D arrays, etc.), and/or have any other arrangement. In an example, the set of neural interface elements can be arranged in a 2D array segmented into a set of neural interface module panels. In a specific example, each neural interface module panel can optionally interface with a corresponding digital controller module panel and/or analog drive module panel. The arrangement of the neural interface elements, routing resources, and/or other circuitry within each neural interface module panel is preferably the same across different neural interface module panels (e.g., each neural interface module panel is identical), but can alternatively be different. In variants, this uniformity can enable high-yield manufacturing of a large array of neural interface elements. In an illustrative example, the neural interface module 100 can include four panels of neural interface modules, wherein each panel includes a 2D array of 64 neural interface elements (e.g., example shown in FIG. 6).

Figure 2A:
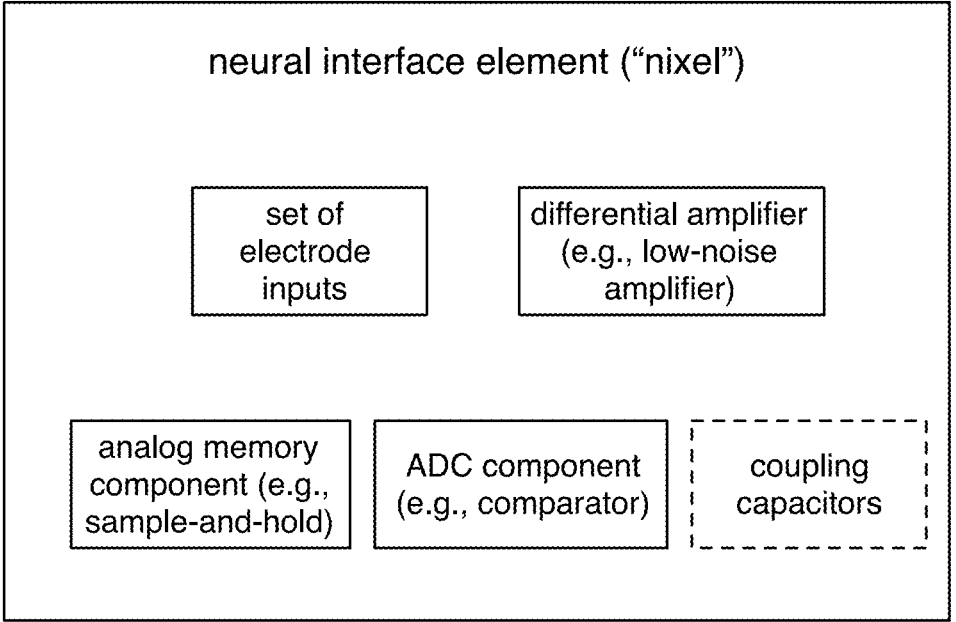
FIG. 2A is a schematic representation of an example of a neural interface element ("nixel").

A neural interface element can include: a set of electrode inputs, routing resources (e.g., one or more electrode input switches coupled to each electrode input), a differential amplifier (e.g., low-noise amplifier (LNA)), analog memory component, an analog-to-digital converter (ADC) component, optional capacitors, and/or any other integrated circuit components. An example is shown in FIG. 2A and FIG. 2B. An electrode input can be an electrode and/or a connector to a separate electrode (e.g., wherein the connector can send and/or receive signals from the separate electrode). The neural interface element can optionally include all or a portion of impedance measurement circuitry (e.g., coupling capacitors, attenuators, etc.), all or a portion of testing circuitry, and/or any other integrated circuit components. The set of electrode inputs preferably includes two electrode inputs, but can alternatively include one, two, or more than three electrode inputs. The set of electrode inputs preferably include active electrode inputs, but can additionally or alternatively include passive electrode inputs. In a specific example, active electrode inputs can be electrode inputs integrated with additional electrical components (e.g., the differential amplifier, analog memory component, etc.). In another specific example, active electrode inputs can be electrode inputs that are configured to receive electrical signals from a set of neurons (e.g., directly and/or via electrodes). In a specific example, passive electrode inputs can be electrode inputs that are not integrated with additional electrical components. In another specific example, passive electrode inputs can be electrode inputs that are configured to receive electrical signals from a reference and/or a test. However, active electrode inputs and passive electrode inputs can be otherwise configured.

Each electrode input in the set of electrode inputs preferably interfaces with a single neuron (e.g., directly or via a separate electrode), but can alternatively interface with multiple neurons and/or any other signal source. The differential amplifier is preferably configured to record a differential signal from two active electrode inputs in the neural interface element, but can additionally or alternatively be configured to record any other signals (e.g., record a differential signal from an active electrode input and a passive electrode input, record a differential signal from two passive electrode inputs, etc.). In a specific example, the polarity of a detected neural signal at the differential amplifier can indicate which electrode input of the two active electrode inputs received the neural signal (e.g., one electrode input corresponds to a positive signal and the other electrode input corresponds to a negative signal). The differential amplifier can optionally be configured according to one or more amplifier settings (e.g., determined by the digital controller). The analog memory component is preferably an analog sample-and-hold that functions as an analog memory, but can alternatively be any other analog memory component. The ADC component is preferably a comparator functioning as the analog front-end of a single-slope ADC, but can additionally or alternatively include components from other ADC types, such as multi-slope, delta-sigma, successive approximation register (SAR), algorithmic, and pipeline ADC, and/or any other ADC type. In a specific example, single-slope counting ADCs can be beneficial as it can use only an analog comparator in the front-end (e.g., using only a globally provided ramp signal), and remaining modules can be implemented in digital domain outside the neural interface element array.

In an example, a low-level neural signal is first amplified using a low-noise amplifier (LNA), then sampled into an analog memory in the form of sample-and-hold amplifier, and then converted directly to a digital signal within the neural interface element using an analog comparator. The comparator can optionally compare sampled analog signal in the analog memory with a globally routed ramp signal. In a specific example, when the stored analog value matches with the ramp value at a given time, the comparator can generate a digital pulse value, corresponding to a voltage-to-time type digital signal. The digital pulse generated by the comparator can then be processed further in the digital domain to convert that pulse to a digital time information, which in turn correlates well with the amplitude of the ramp signal in time. The digital pulse generated by the comparator can then optionally be processed further in the digital domain to convert that pulse to a digital time information, which in turn correlates well with the amplitude of the ramp signal in time. In a specific example, an output from the analog memory component (e.g., analog sample-and-hold) is compared with a digital pulse generated by the comparator. In a specific example, a time of arrival of the digital pulse can be proportional to an amplitude of the output from the analog memory component. In an example, the digital controller module 200 can include a global counter and a digital memory. In a specific example, the digital memory can be configured to store an output of the global counter upon arrival of the digital pulse generated by the comparator.

Thus, a single slope ADC operation can optionally be achieved in a distributed manner, where, in a specific example, analog front-ends can be implemented right in the neural interface elements in the same location as the electrode inputs, remaining digital functions are implemented outside the neural interface element array, and analog ramp generation is implemented in the analog domain outside the array in a local region (e.g., using best practices of analog and mixed-signal design without being limited by the pitch based limitations of the neural interface elements).

All or a portion of the circuit elements can be integrated in a single chip. In variants (e.g., variants that use stacked chip solutions), the signal path can be implemented within the same neural interface element area (e.g., from an electrode input to a digitized signal, including the digital memory and digital processing circuits), but distributed into multiple chip layers.

In a first variant, the neural interface elements can be used to record signals from neurons. For example, the differential amplifier (e.g., LNA) can simultaneously record signals from two electrode inputs, where one electrode input acts as the reference for the other electrode input. For example, the first electrode in the pair of electrode inputs can be used as the reference (e.g., the reference electrode input) at a first time (e.g., while receiving a neural signal from the second electrode input), and the second electrode input in the pair of electrode inputs can be used as the reference at a second time (e.g., while receiving a neural signal from the first electrode input). Amplifier settings can optionally be used to determine which electrode input is used as the reference (e.g., using threshold detection). The amplifier settings are preferably determined by the digital controller module 200, but can be otherwise determined. Amplifier settings can include: gain settings, corner frequency settings (e.g., low pass (LP) corner frequency settings and/or high pass (HP) corner frequency settings, and/or any other amplifier settings. In a specific example, the gain setting can be between 5 V/V and 1000 V/V or any range or value therebetween (e.g., from 13 V/V to 200 V/V). In a specific example, the LP corner frequency setting can be between 0.5 kHz and 50 kHz or any range or value therebetween (e.g., from 1.4 kHz to 14 kHz). In a specific example, the HP corner frequency setting can be between 2 kHz and 1000 kHz or any range or value therebetween (e.g., from 3.8 kHz to 460 kHz). The recorded signal can then be digitized (e.g., using the integrated comparator), optionally multiplexed across multiple neural interface elements, and transmitted to the digital controller module 200 (e.g., to a memory component of the digital controller module 200).

In a second variant, the neural interface elements can be used to deliver signals to electrodes (e.g., for stimulating the neurons, to measure impedance, etc.). For example, an individual active electrode input of a neural interface element can be connected (e.g., via the routing resources) to impedance measurement circuitry (e.g., coupling capacitors, attenuators, etc.), wherein a stimulus signal can be delivered to the active electrode input via the impedance measurement circuitry. In a specific example, the stimulus signal can be: a programmed signal (e.g., an artificial waveform) generated by an SPI in the digital controller module 200. In another specific example, the stimulus signal can be generated using direct digital synthesis. In another specific example, the stimulus signal can be provided via passive electrode inputs (e.g., test electrode inputs). A resulting signal at an active electrode input of a neural interface element electrode input can optionally be recorded for impedance measurement (e.g., via the first variant). In variants, impedance measurements can be used for calibration, testing, and/or other purposes. In a first specific example, one passive electrode input can be used to perform an impedance measurement for every neural interface element (e.g., for each individual active electrode input of the neural interface elements). In a second specific example, one passive electrode input in each panel can be used to perform an impedance measurement for every neural interface element in the corresponding panel. In a third specific example, other passive and/or active electrode inputs in a panel can be used to perform an impedance measurement. The number of impedance measurement circuits in panels and chips can optionally be increased to enable performing impedance measurements in parallel for both electrode inputs of a neural interface element and/or for multiple electrode inputs of multiple neural interface elements.

The neural interface elements can optionally include spike neural interface elements and Local Field Potential (LFP) neural interface elements. spike neural interface elements can optionally be used for neural spike recording applications. LFP neural interface elements can optionally be used for neural LFP signal recording applications. The neural interface module 100 preferably includes more spike neural interface elements than LFP neural interface elements, but can alternatively include fewer or the same number of spike neural interface elements than LFP neural interface elements. In an illustrative example, each neural interface module panel can include 60 spike and 4 LFP neural interface elements (with differential inputs). In a specific example, spike and LFP neural interface elements can have the same integrated recording electronics (e.g., LNA, sample-and-hold, comparator, etc.), but can be operated using different gain settings (e.g., LFPs can use lower gains), LP corner frequency settings, and/or HP corner frequency settings for the respective differential amplifiers (e.g., LNAs). For example, the differential amplifiers of the spike neural interface elements can be operated using a first set of gain settings and a first set of corner frequency settings, and the differential amplifiers of the LFP neural interface elements can be operated using a second set of gain settings and a second set of corner frequency settings. LFP neural interface elements can optionally include electrode inputs with greater capacitance values relative to electrode inputs in the spike neural interface elements. In an example, the LFP neural interface element electrode inputs can have capacitance values that are 2-20 times greater than capacitance values for spike neural interface element electrode inputs or any range or value therebetween (e.g., 5, 10, greater than 10, etc.), but can alternatively be less than 2 or greater than 20 times greater. LFP neural interface elements can optionally include and/or interface with larger coupling capacitors in the respective impedance measurement circuitry relative to coupling capacitors for the spike neural interface elements (e.g., enabling the LFP neural interface elements to use electrode inputs with greater capacitance values).

The neural interface module 100 can optionally include an array of electrode inputs (e.g., an array of electrode input pairs), wherein the integrated recording electronics (e.g., LNA, sample-and-hold, comparator, etc.) for each neural interface element are arranged beneath the respective electrode inputs (e.g., electrode input pair) for the neural interface element. The array of electrode inputs can be connected (directly or indirectly) with neurons, but can additionally or alternatively interface with other tissue, a signal source, measurement devices, and/or any other system. The array of electrode inputs preferably includes active electrode inputs (e.g., electrode inputs in neural interface elements) and passive electrode inputs but can alternatively include only active electrode inputs (e.g., where passive electrode inputs are located elsewhere on the IC) and/or can be otherwise configured. In a specific example, the passive electrode inputs can include one or more reference electrode inputs (e.g., 8 reference electrode inputs) and/or one or more test electrode inputs (e.g., 8 test electrode inputs). In an illustrative example, each neural interface module panel can include 128 electrode inputs recorded differentially using 64 neural interface elements. In an illustrative example, each neural interface module panel can have 22 Rows and 3 columns, including 132 electrode inputs, out of which 128 are active electrode inputs mapped to 64 neural interface elements with recording circuitry, and 4 are passive electrode inputs (e.g., 2 reference electrode inputs and 2 test electrode inputs). In an example, electrode inputs for LFP neural interface elements can be arranged adjacent to passive electrode inputs in the electrode input array. In a specific example, the (larger) coupling capacitors of the LFP neural interface elements can be partially or completely located beneath the passive electrode inputs (e.g., in the extra space beneath the passive electrode inputs due to the absence of all or a portion of integrated recording electronics normally associated with the active electrode inputs).

Routing resources can function to connect individual neural interface elements and/or components therein (e.g., electrode inputs, LNAs, comparators, etc.) to other system components. The routing resources can additionally or alternatively function to connect passive electrode inputs and/or any other neural interface module 100 components to other system components. The routing resources can include connections (e.g., wires) and/or programmable switches. The routing resources preferably include connections to each individual neural interface element, but can alternatively include connections to a subset of neural interface elements, a group of neural interface elements, and/or can be otherwise connected to one or more neural interface elements. In variants, the transistor switches used in the routing resources can provide protection against antenna events during CMOS fabrication or electrostatic discharge (ESD) protection during assembly and/or operation of one or more capacitors in neural interface elements (e.g., which are known to be sensitive to such events). In a specific example, the neural interface module 100 does not include any additional ESD protection circuits other than the above mentioned switches attached to the neural interface element inputs.

In an example, the routing resources can be used to switch between operating modes of the system 10 and/or a component therein. For example, the system 10 can be configured to operate in one or more modes, such as: a fully differential mode, a single-ended mode, a test mode, and/or a stimulus mode. In a first example, the system 10 operating in a fully differential mode can record a differential signal from two neurons using a neural recording element (e.g., where one electrode input in the pair of electrode inputs acts as a reference for the other electrode input). In a second example, the system 10 operating in a single-ended mode can record a signal from a single neuron using a neural recording element (e.g., wherein a global passive electrode input is used as the reference). In a third example, the system 10 operating in a test mode can apply test signals to the electrode inputs (e.g., to characterize the electrode input interface in terms of impedance levels at various frequencies and amplitude levels). In a specific example, in the test mode, the neural interface module 100 can be configured to amplify and digitize the test signal using the main recording signal path of the neural interface module 100 (e.g., from the differential amplifier to digital data ports); additionally or alternatively, the neural interface module 100 can route the test signal to an analog test output using an integrated analog multiplexer. In a fourth example, the system 10 operating in a stimulus mode can deliver signals to neurons (e.g., for stimulating the neurons, to measure impedance, etc.). In a specific example, a stimulus signal generated by a programmable voltage-output DAC (v-DAC) of the analog drive module can be applied to an individual active electrode input of a neural interface element via an internal coupling capacitor in the neural interface element. The resulting signal at the electrode input can optionally be recorded digitally (e.g., by the main recording signal path of the neural interface module 100), and/or be routed back to analog test outputs (e.g., to calibrate impedance measurement circuits).

Figure 4:
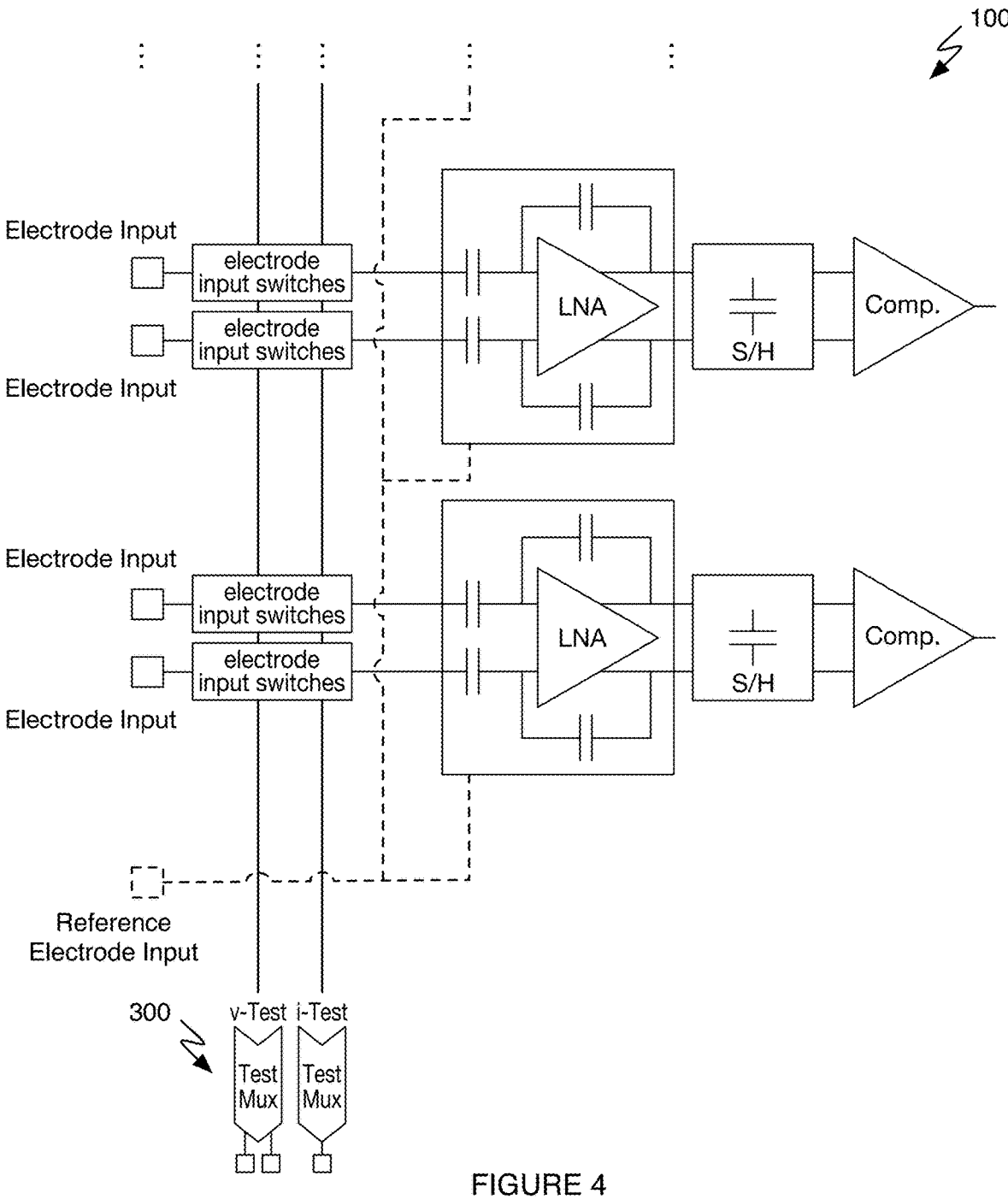
FIG. 4 depicts an example of a set of neural interface elements.

In a first variant, the routing resources can provide connections to active electrode inputs (e.g., to every active electrode input across the set of neural interface elements). For example, the routing resources can include electrode input switches (e.g., an analog switch matrix, a multiplexer, any other switching circuitry, etc.); an example is shown in FIG. 4. In an example, the switches can connect electrode inputs to differential amplifiers (e.g., as described in the second variant). For example, each neural interface element can include: a first electrode input switch (e.g., a first analog switch-matrix) coupled capacitively to a first electrode input; and a second electrode input switch (e.g., a second analog switch-matrix) coupled capacitively to a second electrode input. In a first specific example, the first electrode input switch and/or the second electrode input switch can be configured to change an input polarity of the differential amplifier. In a second specific example (e.g., in a single-ended mode and/or a test mode), an electrode input switch can be configured to disconnect an input of the differential amplifier from an active electrode input and/or connect the input to a third electrode input (e.g., a passive electrode input). In a fourth specific example (e.g., in a test mode), an electrode input switch can be configured to connect an active electrode input to an impedance measurement circuit (e.g., without disconnecting the active electrode input from the LNA input). The impedance measurement circuit can optionally be the same as and/or connected to the testing circuit. In a fifth specific example (e.g., in a stimulus mode), an electrode input switch can connect an active electrode input to one or more coupling capacitors, which can be used to deliver a stimulus signal to the active electrode input. The coupling capacitors can optionally be connected (e.g., via routing resources) to one or more analog drive components (e.g., voltage DACs used in the testing circuitry, etc.) and/or any other system components (e.g., using SPI programming provided by the digital controller module 200).

In a second variant, the routing resources can provide connections to differential amplifiers (e.g., to every LNA across the set of neural interface elements). In a first example, routing resources can connect the LNA input to one or both active electrode inputs in the neural interface element. In a second example, the routing resources can connect the LNA to other signals (e.g., and optionally disconnect the LNA from one or more active electrode inputs). In a first specific example, the LNA input can be connected to one or more passive electrode inputs (e.g., a globally routed test and/or reference signals, generated on-chip or externally). In an illustrative example, a reference electrode input (e.g., global reference electrode input for the neural interface module panel) can be used as the reference signal for the differential LNA instead of the second active electrode input. In a second specific example, the LNA can be connected to a static bias voltage generated by the analog drive module 300 (e.g., via the voltage-output DAC, etc.).

In an example, switches and/or other routing resources can connect an electrode input to the differential amplifier (e.g., LNA) input. In a specific example, the switches can determine the polarity of the input signal applied to the LNA inputs. The switches can be configured to perform A-B, B-A, A-R, R-B, A-T, T-B, A-G, G-A, B-G, G-B, and G-G type arithmetic functions right at the input of the LNA, where A and B are signal names at two neural interface element electrode inputs, R is the reference signal connected to spike or LFP neural interface elements, Tis one of the globally available test inputs coming either from test electrode inputs or locally generated signals from analog drive module, and G is signal ground used on-chip. As can be seen here, the switches at the neural interface element inputs can perform a rich set of arithmetic functions that can be quite valuable during testing this chip during assembly tests or on the fly when in use in an implant. It should be noted that in pseudo differential operation, when externally provided references turn out to be not low-noise enough, using signal ground of the chip as a reference (e.g., A-G or B-G switch configuration) may provide better overall noise. To determine the ultimate noise performance of the LNA, both inputs can optionally be connected to signal ground (e.g. using G-G switch configuration) to measure noise performance of the LNA.

Figure 5B:
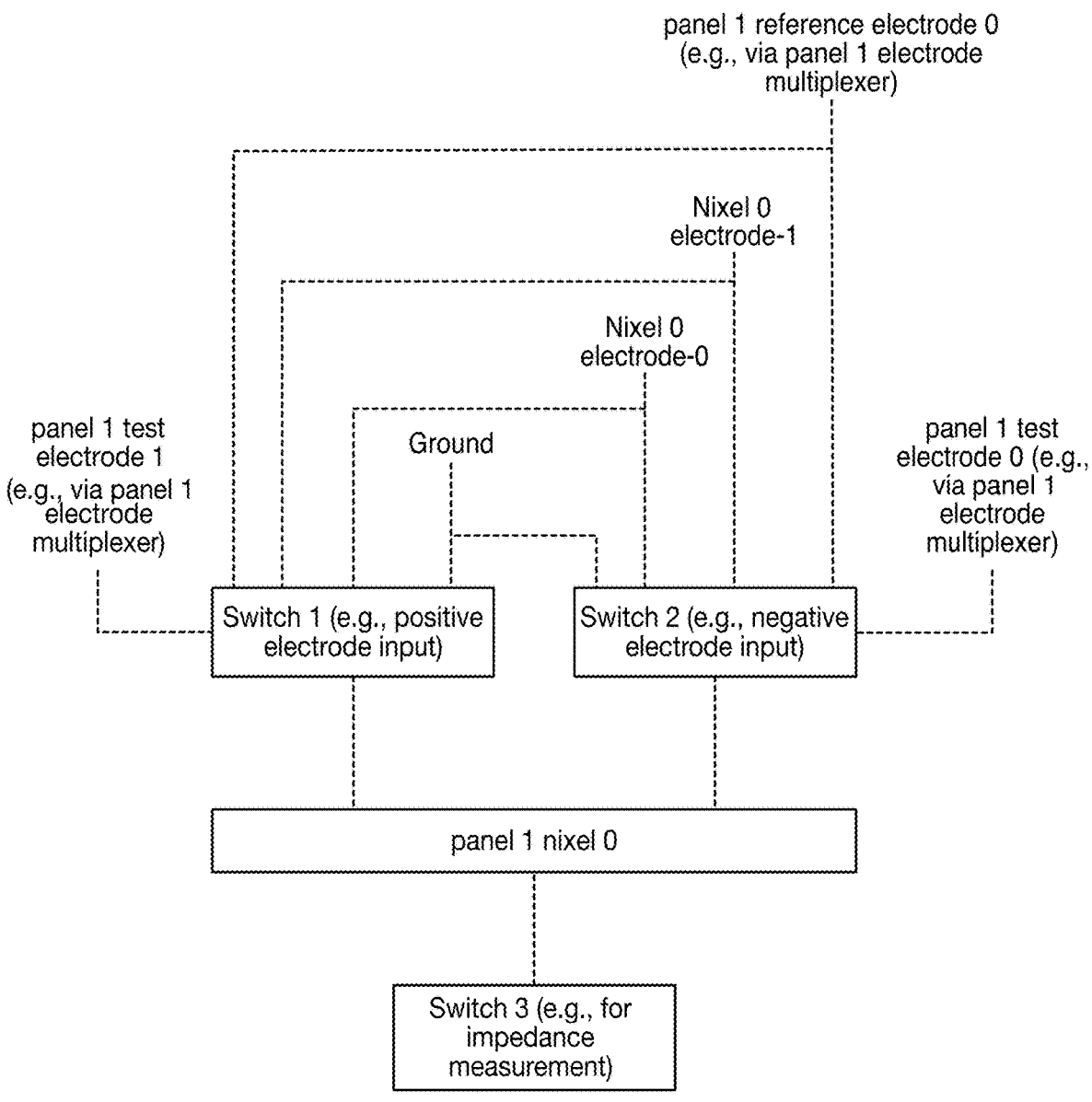
FIG. 5B depicts an example of a neural interface element ("nixel") in a panel of the system.

In an example, there can be one or more switches for every neural interface element. An example is shown in FIG. 5B. In a specific example, a switch (e.g., Switch 1) can be used for the positive electrode input of the LNA of the neural interface element. In another specific example, a switch (e.g., Switch 2) can be used for the negative electrode input of the LNA of the neural interface element. In another specific example, a switch (e.g., Switch 3) can be used for the Impedance Measurement. Switches can optionally be independently configured. In an illustrative example, the possible input configurations for Switch 1 can include: Panel Test Electrode Input 1 (e.g., PTE-1), the Panel Reference Electrode Input (PRE), Nixel Electrode Input-0, Nixel Electrode Input-1, and/or Ground (GND). In an illustrative example, the possible input configurations for Switch 2 can include: Panel Test Electrode Input 0 (e.g., PTE-0), the Panel Reference Electrode Input (PRE), Nixel Electrode Input-0, Nixel Electrode-1, and/or Ground (GND). The Switch 1 and Switch 2 configuration can optionally allow the following analog arithmetic functions at the LNA inputs: Panel Test Electrode Input-0 MINUS Panel Test Electrode Input-1; Panel Test Electrode Input-0 MINUS Nixel Electrode Input-1; Nixel Electrode Input-0 MINUS Nixel Electrode Input-1; Nixel Electrode Input-0 MINUS Panel Reference Electrode Input; Nixel Electrode Input-0 MINUS Panel Test Electrode Input-1; Nixel Electrode Input-0 MINUS Ground; Nixel Electrode Input-1 MINUS Nixel Electrode Input-0; Nixel Electrode Input-1 MINUS Panel Reference Electrode Input; Nixel Electrode Input-1 MINUS Panel Test Electrode Input-1; Nixel Electrode Input-1 MINUS Ground; Ground MINUS Ground. The polarity of the measurement can be changed with these possible switch configurations without switching the electrode input connections on the outside. A neural interface module panel can optionally include two Panel Reference Electrode Inputs (e.g., one for the LFP neural recording elements and another for the spike neural recording elements). In a specific example, for a given neural interface element in a panel, there is only one available reference input for LNA inputs. In variants, possible input switch configurations can allow various input configurations without the need for changing the electrode input connections at the LNA inputs, Panel Test or Reference inputs. In an example, the Panel Test Electrode Input-0/1 and Panel Reference Electrode Input-0/1 can have options to be disconnected from the associated electrode inputs, and instead to be driven by the dedicated Voltage DACs in the Analog Drive Circuit. In that case, switching the DAC contents using serial programming can also allow polarity switching without changing any of these switch configurations.

In a third variant, the routing resources can provide connections to ADC components (e.g., to every comparator across the set of neural interface elements). In a specific example, an output from the comparator can be routed to the digital controller module 200 (e.g., to the neural interface element memory component) using routing resources integrated in the neural interface elements. This routing resource can enable various logic operations and/or injecting test signals controlled by the digital controller module 200. These features can become especially useful in determining the functionality of the neural interface elements during device assembly as well as normal use in an implant. In the latter case, such tests can enable quick assessment of the existence of proper electrode connection for an implant.

In a fourth variant, the routing resources can provide connections to passive electrode inputs. In a first specific example, the routing resources can connect a reference electrode input to one or more LNAs (e.g., in parallel). In an illustrative example, a global panel reference electrode input can be connected to each neural interface element LNA in the panel. In a second specific example, the routing resources can connect one or more passive electrode inputs to analog drive module components (e.g., testing circuitry). This can enable driving the passive electrode inputs using on-chip test voltages generated by the analog drive module. It also makes it possible to monitor these signals during tests for calibration and/or verification purposes. As a specific example, during impedance measurement, using just the analog test outputs enables performing efficient impedance measurement tests without relying on an integrated signal chain of the neural interface elements for quick verification and/or calibration purposes.

In a fifth variant, a combination of the previous variants can be used to connect components of the system.

However, the neural interface module 100 can be otherwise configured.

4.2. Digital Controller Module 200

The system 10 can optionally include a digital controller module 200, which functions to control data transfer, generate digital configuration and/or timing signals for the analog and digital modules in the chip (e.g., for the set of neural interface elements, the analog drive module 300, and the digital controller module 200), and/or perform data processing (e.g., thresholding, on-chip compression, etc.). In an example, in the neural interface module 100, the digital controller module 200 can function to generate static configuration settings that define gain and frequency corners of the differential amplifiers, and/or define static configuration settings of the electrode input switches. For example, in the analog drive module 200, the digital controller module 200 can function to provide digital control signals for programmable voltage and bias settings, analog multiplexers for internal test and routing resources, and/or timing signals for the ramp generator block. For example, within the digital controller module 200, the digital controller module 200 can control data transfer from the SPI to the local registers that hold the chip settings, provide timing for the scanning of neural interface element memories for data output, and/or provide timing and synchronization signals between core logic and serialized data ports.

The digital controller module 200 can include one or more of: digital controllers, memory components (e.g., within the digital controller and/or separate from the digital controller), serializers, serial programming interface (SPI), input/output (I/O) buffers, I/O ports, register arrays, timing state machines, and/or any other IC components. All or a portion of the digital controller module 200 can optionally be segmented into digital controller module panels (e.g., corresponding to the neural interface module panels). In an example, registers in the digital controller module 200 can be portioned into functional groups (e.g., biasing, configuration, timing, etc.). In a specific example, biasing registers can control the voltage and current drive levels of all programmable biasing resources on the chip. In an example, a timing state machine in the digital controller module 200 can generate digital timing signals used as timing signals in the chip (e.g., in analog blocks such as the neural interface element array and ramp generator; in digital blocks such as neural interface element memory and its digital readout, and serializers at the data ports; etc.). For example, the digital controller module 200 can generate digital timing signals for each panel of neural interface elements (e.g., the digital controller module 200 can include or use one counter for each panel). In a specific example, for each neural interface element within a panel of neural interface elements, the arrival time of the digital signal coming from the comparator of the neural interface element can capture the panel counter value, which corresponds to digital representation of the analog value of the output of the sample-and-hold block storing the amplified version of the analog input signal. In a specific example, the analog input value of the neural recording elements can be converted to the digital codes based on the arrival times of the comparator outputs of the neural recording elements. In an illustrative example, that the time position of a stored digital datapoint can be used to identify the amplitude and polarity of the analog input signal of the neural interface element that recorded the datapoint, which can be used to identify the specific electrode input the spike data is coming from (of the pair of electrode inputs used in the differential neural interface element) for that recorded the datapoint.

In a first variant, the digital controller module 200 can receive, store, and/or output neural signals recorded by the neural interface module 100. For example, digitized recorded neural signals can be received and stored by a memory component (e.g., within the digital controller or separate from the digital controller), optionally multiplexed with other recorded neural signals, transmitted to the digital controller and/or components therein, serialized (via a serializer), transmitted to an I/O buffer, and output via one or more I/O ports. In a second variant, the digital controller module 200 can receive, store, and/or output supplementary signals (e.g., recorded by a supplementary device). For example, data can be received, stored, output, and/or otherwise processed by the SPI ports. In a third variant, the digital controller module 200 can generate and/or transmit signals. For example, an arbitrary waveform (e.g., arbitrary waveforms with any amplitude and frequency) can be programmed by the SPI and transmitted to one or more voltage DACs to generate analog representation of digitally provided signals, to be used as test inputs for various tests and measurements, such as impedance measurement. In a fourth variant, the digital controller module 200 can be used to determine and/or implement settings for one or more system components (e.g., routing resources, amplifier, memory components, etc.). Settings can include: amplifier settings, bias settings, configuration settings (e.g., routing settings; programming the switches to determine routing configuration), timing settings (e.g., defining sampling rate of recording channels), and/or any other settings. In a specific example, bias settings can determine the voltage output by the voltage-output DAC, current output by the current-output DAC, and/or any other bias settings. Bias settings can optionally be changed on-the-fly. In a fifth variant, a combination of the previous variants can be implemented.

However, the digital controller module 200 can be otherwise configured.

4.3. Analog Drive Module 300

The system 10 can optionally include an analog drive module 300 (e.g., bias generator module), which functions to generate bias voltages and/or bias currents (e.g., for differential amplifiers and/or ADC components in the neural interface module 100), deliver signals to electrode inputs in the neural interface module 100 (e.g., for impedance measurement, for stimulating neurons, etc.), perform direct measurements of the electrode inputs (e.g., for testing purposes), and/or otherwise function. The analog drive module 300 can be connected to the neural interface module 100, the digital controller module 200, and/or any other system components.

The analog drive module 300 can include one or more: ramp generators, bandgap voltage references (BandGap V-Ref), regulators, voltage-output digital-to-analog converters (v-DAC), current-output digital-to-analog converters (i-DAC), all or a portion of impedance measurement circuitry (e.g., coupling capacitors, attenuators, etc.), all or a portion of testing circuitry, and/or any other IC components. All or a portion of the analog drive module 300 (e.g., commonly used blocks, such as bandgap voltage reference, seed-current generation circuits, etc.) can optionally be instantiated only once in the entire chip, All or a portion of the analog drive module 300 can be integrated per panel (e.g., to provide better drive for panels with less loading and undesired coupling).

The bandgap voltage reference can function to generate a voltage (e.g., supply and temperature independent voltage) that can optionally be provided to the regulator. The regulator can function to generate a reference voltage that optionally can be provided to one or more DACs. The voltage-output DAC (v-DAC) can function to generate a reference voltages (e.g., according to bias settings), which can optionally be provided to the differential amplifier (e.g., LNA) and/or the ADC component (e.g., comparator) in each neural interface element. The current-output DAC (i-DAC) can function to generate a supply independent bias currents (e.g., according to bias settings), which can optionally be provided to the differential amplifier (e.g., LNA) and/or the ADC component (e.g., comparator) in each neural interface element. One or more v-DACs and i-DACs can be used for analog blocks used in the neural interface module 100 and/or any other analog system components.

Testing circuitry can function to connect internal analog nodes to test pads to test their values against expected levels, based on system defaults or SPI programming levels. v-DACs and i-DACs can be tested by connecting their representative outputs to one of the available voltage test outputs. There can optionally be a dedicated current test output that allows termination to ground or supply potentials using a certain value resistor to convert i-DAC outputs to voltage for easy measurement. The test circuitry can optionally allow routing the critical analog signals such as ramp generator output to the test pads, so that one can perform an ADC characterization starting from analog input to the digital outputs in terms of ADC parameters, such as input range, integral non-linearity (INL), differential non-linearity (DNL), and/or any other ADC parameters. However, testing circuitry can be otherwise configured.

However, the analog drive module 300 can be otherwise configured.

4.4. Electrode Multiplexer 400

The system 10 can optionally include an electrode multiplexer 400, which can function to connect the neural interface module 100 to the analog drive module 300. Additionally or alternatively, the electrode multiplexer 400 can function to connect passive electrode inputs in the neural interface module 100 to neural interface elements in the neural interface module 100. The electrode multiplexer 400 can optionally be segmented into a set of panels (e.g., the system can include one electrode multiplexer circuit for each system panel) to reduce the capacitive loading of the global routing resources in the chip or to be able to reduce number of active recording channels working in parallel.

In a first variant, the electrode multiplexer 400 can route panel specific global reference inputs to neural interface elements in the corresponding panel. For example, the panel specific global reference inputs for a panel can include two reference electrode inputs in the panel. In a specific example, one reference is used for Local Field Potential (LFP) neural interface elements, and another reference is used for spike detection neural interface elements. The electrode multiplexer 400 can optionally disconnect the panel specific global reference inputs from the neural interface elements and instead drive the neural interface elements with reference signals generated on-chip in the analog drive module 300. In a specific example, the analog drive module 300 generates 2 such global reference signals (e.g., only 2 global reference signals), that can be routed to the inputs of all of the electrode multiplexer 400 (e.g., across the panels).

In a second variant, the electrode multiplexer 400 can route panel specific global test inputs to neural interface elements in the corresponding panel. For example, the panel specific global test inputs for a panel can include two test electrode inputs in the panel. In a specific example, these test inputs can be routed as pairs to every neural interface element in the panel providing fully differential testing capability. The electrode multiplexer 400 can optionally disconnect the global test inputs and instead drive the neural interface elements with electrode input test signals generated on-chip in the analog drive module 300. In a specific example, the analog drive module 300 generates 2 such global test signals (e.g., only 2 test reference signals), that can be routed to the inputs of all of the electrode multiplexer circuits 400 (e.g., across the panels).

In a third variant, the electrode multiplexer 400 can route a dedicated test signal for impedance measurement signal, generated on-chip in the analog drive module 300. The system can readout the result of impedance measurement test digitally using a signal path integrated on chip, from every neural interface element input to the digital serial data ports. The electrode multiplexer 400 can optionally be used to readout the result of an impedance measurement test in analog domain, by routing the signal seen at the neural interface element inputs back to the analog test outputs. This analog impedance measurement test can be used to calibrate the digital impedance measurement test, using calibrated external test equipment. Using the analog impedance measurement test can also allow continuous time characterization of impedance measurement circuits without any limitations on signal resolution and bandwidth.

However, the electrode multiplexer 400 can be otherwise configured.

However, the system 10 can be otherwise configured.

6. Specific Examples

A numbered list of specific examples of the technology described herein are provided below. A person of skill in the art will recognize that the scope of the technology is not limited to and/or by these specific examples.

Specific Example 1. An integrated circuit system, comprising: a neural interface module comprising an array of neural interface elements, wherein each neural interface element comprises: a first electrode input configured to receive a signal from a first neuron; a second electrode input configured to receive a signal from a second neuron; a differential low-noise amplifier configured to record a differential signal from the first electrode input and the second electrode input, wherein one of the first electrode input or the second electrode input is used as a reference; and an analog sample-and-hold configured to store the signal from the low-noise amplifier.

Specific Example 2. The integrated circuit system of Specific Example 1, wherein each neural interface element further comprises a comparator, wherein an output from the analog sample-and-hold is compared with a digital pulse generated by the comparator, wherein a time of arrival of the digital pulse is proportional to an amplitude of the output from the analog sample-and-hold.

Specific Example 3. The integrated circuit system of Specific Example 2, further comprising a digital controller module comprising a global counter and a digital memory, wherein the digital memory is configured to store an output of the global counter upon arrival of the digital pulse generated by the comparator.

Specific Example 4. The integrated circuit system of Specific Example 3, wherein the array of neural interface elements comprises multiple panels of neural interface elements, wherein the digital controller module generates digital timing signals for each panel of neural interface elements.

Specific Example 5. The integrated circuit system of Specific Example 4, wherein, for each neural interface element within a panel of neural interface elements, the digital signal from the comparator of the neural interface element is stored at a time position corresponding to the neural interface element.

Specific Example 6. The integrated circuit system of any of Specific Examples 1-5, wherein each neural interface element further comprises: a first analog switch-matrix coupled capacitively to the first electrode input; and a second analog switch-matrix coupled capacitively to the second electrode input.

Specific Example 7. The integrated circuit system of Specific Example 6, wherein the first analog switch-matrix is configured to change an input polarity of the differential low-noise amplifier.

Specific Example 8. The integrated circuit system of any of Specific Examples 6-7, wherein the first analog switch-matrix is configured to disconnect an input of the differential low-noise amplifier from the first electrode input.

Specific Example 9. The integrated circuit system of Specific Example 8, wherein the first analog switch-matrix is further configured to connect an input of the differential low-noise amplifier to a third electrode input.

Specific Example 10. The integrated circuit system of any of Specific Examples 1-9, wherein the neural interface module comprises at least 256 neural interface elements.

Specific Example 11. The integrated circuit system of any of Specific Examples 1-10, wherein the neural interface module further comprises a set of reference electrode inputs and a set of test electrode inputs.

Specific Example 12. The integrated circuit system of any of Specific Examples 1-11, wherein the array of neural interface elements comprises a first subset of neural interface elements configured for neural spike recording and a second subset of neural interface elements configured for neural Local Field Potential (LFP) recording.

Specific Example 13. The integrated circuit system of any of Specific Examples 12, wherein the differential low-noise amplifiers of the first subset of neural interface elements are operated using a first set of gain settings and a first set of corner frequency settings, and wherein the differential low-noise amplifiers of the second subset of neural interface elements are operated using a second set of gain settings and a second set of corner frequency settings.

Specific Example 14. The integrated circuit system of any of Specific Examples 12-13, wherein each neural interface element comprises a coupling capacitor, wherein the second subset of neural interface elements comprise different coupling capacitors than the first subset of neural interface elements.

Specific Example 15. The integrated circuit system of any of Specific Examples 12-14, wherein the neural interface module further comprises a set of passive electrode inputs, wherein the second subset of neural interface elements are arranged adjacent to the set of passive electrode inputs.

Specific Example 16. The integrated circuit system of Specific Example 15, wherein the coupling capacitors of the second subset of neural interface elements are arranged beneath the set of passive electrode inputs.

Specific Example 17. The integrated circuit system of any of Specific Examples 1-16, wherein, for each neural interface element, the first electrode input and the second electrode input are arranged above the differential low-noise amplifier and/or sample-and-hold capacitor.

Specific Example 18. The integrated circuit system of any of Specific Examples 1-17, wherein, at a first time, the first electrode input is used as the reference, and wherein, at a second time, the second electrode input is used as the reference.

Specific Example 19. The integrated circuit system of any of Specific Examples 1-18, further comprising determining an amplitude and polarity of the differential signal; and associating the differential signal with one of the first electrode input or the second electrode input based on the polarity of the differential signal.

Specific Example 20. The integrated circuit system of any of Specific Examples 1-19, further comprising a digital controller module configured to determine settings for each neural interface element, the settings comprising at least one of: bias settings, timing settings, or configuration settings.

Specific Example 21. The integrated circuit system of any of Specific Examples 1-20, further comprising an analog drive module configured to generate programmable bias voltages and currents for the neural interface module.

Specific Example 22. A system, comprising: an array of electrode pairs positioned at a first end of a substrate, the array of electrode pairs interfacing with a set of neurons, wherein each electrode pair comprises: a first electrode configured to receive an electrical signal from a first neuron in the set of neurons; and a second electrode configured to receive an electrical signal from a second neuron in the set of neurons; and an integrated circuit positioned at a second end of the substrate, the integrated circuit comprising an array of neural interface elements, wherein each neural interface element is configured to record a differential signal from a corresponding electrode pair in the array of electrode pairs.

Specific Example 23. The system of Specific Example 22, wherein the set of neurons comprise optogenetically modified neurons, the system further comprising: an array of LEDs positioned at the first end of a substrate, the array of LEDs configured to transmit light signals to set of neurons; and a second integrated circuit positioned at the second end of the substrate, the second integrated circuit configured to drive the array of LEDs.

Specific Example 24. The system of Specific Example 23, wherein the integrated circuit comprises at least 200 neural interface elements, wherein the second integrated circuit comprises at least 200 LEDs.

Specific Example 25. The system of any of Specific Examples 23-24, wherein the array electrode pairs are arranged in a first two-dimensional (2D) grid, wherein the array of LEDs are arranged in a second 2D grid overlapping with the first 2D grid, wherein the second 2D grid is staggered relative to the first 2D grid.

Specific Example 26. The system of any of Specific Examples 23-25, wherein an LED in the array of LEDs transmits a light signal to a neuron of interest, and wherein an electrode in the array of electrode pairs receives an electrical signal from the neuron of interest.

Specific Example 27. The system of any of Specific Examples 23-26, wherein a distance between an LED of the array of LEDs and an electrode of the array of electrode pairs is between 25 μm and 100 μm.

Specific Example 28. The system of any of Specific Examples 22-27, wherein each electrode pair comprises adjacent electrodes in the array of electrode pairs, wherein a distance between the adjacent electrodes is between 50 μm and 200 μm.

Specific Example 29. The system of any of Specific Examples 22-28, wherein the array of electrodes is implanted within a brain.

Specific Example 30. The system of any of Specific Examples 22-29, wherein the array of electrodes is implanted on a surface of a brain.

Specific Example 31. The system of any of Specific Examples 22-30, further comprising a cell container arranged above the array of electrodes, wherein the set of neurons are cultured within the cell container.

Specific Example 32. The system of any of Specific Examples 22-31, wherein the substrate comprises a flexible substrate, the flexible substrate comprising multiple polyimide layers.

Specific Example 33. The system of any of Specific Examples 22-32, wherein the substrate comprises a rigid substrate, the rigid substrate comprising polyimide and metal.

Specific Example 34. The system of any of Specific Examples 22-33, wherein a distance between the array of electrodes and the integrated circuit is at least 20 mm.

Specific Example 35. The system of any of Specific Examples 22-34, wherein each neural interface element comprises: a pair of electrode inputs connected to the corresponding electrode pair; a differential low-noise amplifier configured to record the differential signal from the pair of electrode inputs; an analog memory component configured to store the signal from the low-noise amplifier; and a comparator configured to digitize an output from the analog sample-and-hold.

Specific Example 36. The system of Specific Example 35, wherein, each neural interface element further comprises: a first analog switch-matrix coupled capacitively to a first electrode input of the pair of electrode inputs; and a second analog switch-matrix coupled capacitively to a second electrode input of the pair of electrode inputs.

Specific Example 37. The system of Specific Example 36, further comprising a global reference electrode input, wherein, when the system is operating in a single-ended mode, the first analog switch-matrix is configured to: disconnect an input of the differential low-noise amplifier from the first electrode input; and connect an input of the differential low-noise amplifier to the global reference electrode input.

Specific Example 38. The integrated circuit system of any of Specific Examples 22-37, wherein, at a first time, a first electrode of the corresponding electrode pair is used as a reference for a second electrode of the corresponding electrode pair, and wherein, at a second time, the second electrode is used as a reference for the first electrode.

Specific Example 39. The system of any of Specific Examples 22-38, wherein the array of neural interface elements comprises a first subset of neural interface elements configured for neural spike recording and a second subset of neural interface elements configured for neural Local Field Potential (LFP) recording.

Specific Example 40. The system of Specific Example 39, wherein each neural interface element comprises a coupling capacitor, wherein the second subset of neural interface elements comprise larger coupling capacitors than the first subset of neural interface elements.

Specific Example 41. The system of Specific Example 40, wherein the system further comprises a set of passive electrode inputs, wherein the second subset of neural interface elements are arranged adjacent to the set of passive electrode inputs, wherein the coupling capacitors of the second subset of neural interface elements are arranged beneath the set of passive electrode inputs.

All references cited herein are incorporated by reference in their entirety, except to the extent that the incorporated material is inconsistent with the express disclosure herein, in which case the language in this disclosure controls.

As used herein, "substantially" or other words of approximation can be within a predetermined error threshold or tolerance of a metric, component, or other reference, and/or be otherwise interpreted.

Different subsystems and/or modules discussed above can be operated and controlled by the same or different entities. In the latter variants, different subsystems can communicate via: APIs (e.g., using API requests and responses, API keys, etc.), requests, and/or other communication channels. Communications between systems can be encrypted (e.g., using symmetric or asymmetric keys), signed, and/or otherwise authenticated or authorized.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A system, comprising:
an array of electrode pairs positioned at a first end of a substrate, the array of electrode pairs interfacing with a set of neurons, wherein each electrode pair comprises: a first electrode configured to receive an electrical signal from a first neuron in the set of neurons; and a second electrode configured to receive an electrical signal from a second neuron in the set of neurons; and
an integrated circuit positioned at a second end of the substrate, the integrated circuit comprising an array of neural interface elements, wherein each neural interface element is configured to record a differential signal from a corresponding electrode pair in the array of electrode pairs, wherein a distance between the array of electrode pairs and the integrated circuit is at least 20 mm.

2. The system of claim 1, wherein the array of electrode pairs is implanted within a brain.

3. The system of claim 1, wherein the array of electrode pairs is implanted on a surface of a brain.

4. The system of claim 1, wherein the substrate comprises a flexible substrate, the flexible substrate comprising multiple polyimide layers.

5. The system of claim 1, wherein each neural interface element comprises:
a pair of electrode inputs connected to the corresponding electrode pair;
a differential low-noise amplifier configured to record the differential signal from the pair of electrode inputs;
an analog memory component configured to store the signal from the low-noise amplifier; and
a comparator configured to digitize an output from the analog memory component.

6. The system of claim 5, wherein each neural interface element further comprises:
a first analog switch-matrix coupled capacitively to a first electrode input of the pair of electrode inputs; and
a second analog switch-matrix coupled capacitively to a second electrode input of the pair of electrode inputs.

7. The system of claim 6, further comprising a global reference electrode input, wherein, when the system is operating in a single-ended mode, the first analog switch-matrix is configured to: disconnect an input of the differential low-noise amplifier from the first electrode input; and connect an input of the differential low-noise amplifier to the global reference electrode input.

8. The system of claim 1, wherein, at a first time, a first electrode of the corresponding electrode pair is used as a reference for a second electrode of the corresponding electrode pair, and wherein, at a second time, the second electrode is used as a reference for the first electrode.

9. The system of claim 1, wherein the array of neural interface elements comprises a first subset of neural interface elements configured for neural spike recording and a second subset of neural interface elements configured for neural Local Field Potential (LFP) recording.

10. The system of claim 9, wherein each neural interface element comprises a coupling capacitor, wherein the second subset of neural interface elements comprise larger coupling capacitors than the first subset of neural interface elements.

11. The system of claim 10, wherein the system further comprises a set of passive electrode inputs, wherein the second subset of neural interface elements are arranged adjacent to the set of passive electrode inputs, wherein the coupling capacitors of the second subset of neural interface elements are arranged beneath the set of passive electrode inputs.

12. A system, comprising:
an array of electrode pairs positioned at a first end of a substrate, the array of electrode pairs interfacing with a set of neurons, wherein each electrode pair comprises: a first electrode configured to receive an electrical signal from a first neuron in the set of neurons; and a second electrode configured to receive an electrical signal from a second neuron in the set of neurons, wherein the set of neurons comprise optogenetically modified neurons;
an integrated circuit positioned at a second end of the substrate, the integrated circuit comprising an array of neural interface elements, wherein each neural interface element is configured to record a differential signal from a corresponding electrode pair in the array of electrode pairs;
an array of LEDs positioned at the first end of a substrate, the array of LEDs configured to transmit light signals to set of neurons; and
a second integrated circuit positioned at the second end of the substrate, the second integrated circuit configured to drive the array of LEDs.

13. The system of claim 12, wherein the integrated circuit comprises at least 200 neural interface elements, wherein the second integrated circuit comprises at least 200 LEDs.

14. The system of claim 12, wherein the array electrode pairs are arranged in a first two-dimensional (2D) grid, wherein the array of LEDs are arranged in a second 2D grid overlapping with the first 2D grid, wherein the second 2D grid is staggered relative to the first 2D grid.

15. The system of claim 14, wherein a distance between an LED of the array of LEDs and an electrode of the array of electrode pairs is between 25 $\mu$m and 100 $\mu$m.

16. The system of claim 12, wherein an LED in the array of LEDs transmits a light signal to a neuron of interest, and wherein an electrode in the array of electrode pairs receives an electrical signal from the neuron of interest.

17. A system, comprising:
an array of electrode pairs positioned at a first end of a substrate, the array of electrode pairs interfacing with a set of neurons, wherein each electrode pair comprises: a first electrode configured to receive an electrical signal from a first neuron in the set of neurons; and a second electrode configured to receive an electrical signal from a second neuron in the set of neurons, wherein each electrode pair comprises adjacent electrodes in the array of electrode pairs, wherein a distance between the adjacent electrodes is between 50 $\mu$m and 200 $\mu$m; and
an integrated circuit positioned at a second end of the substrate, the integrated circuit comprising an array of neural interface elements, wherein each neural interface element is configured to record a differential signal from a corresponding electrode pair in the array of electrode pairs.

18. The system of claim 17, further comprising a cell container arranged above the array of electrode pairs, wherein the set of neurons are cultured within the cell container.

19. The system of claim 17, wherein the substrate comprises a rigid substrate, the rigid substrate comprising polyimide and metal.

\*  \*  \*  \*  \*